(12) United States Patent
Yokoyama et al.

(10) Patent No.: US 8,168,407 B2
(45) Date of Patent: May 1, 2012

(54) METHOD OF SYNTHESIZING A SUPPRESSOR TRNA, DNA CONSTRUCT AND USE THEREOF FOR PRODUCING A PROTEIN INCLUDING A NON-NATURAL AMINO ACID

(75) Inventors: Shigeyuki Yokoyama, Yokohama (JP); Kensaku Sakamoto, Yokohama (JP); Nobumasa Hino, Yokohama (JP); Takahito Mukai, Yokohama (JP); Takatsugu Kobayashi, Yokohama (JP)

(73) Assignee: Riken, Wako-shi, Saitama (JP)

( * ) Notice: Subject to any disclaimer, the term of this patent is extended or adjusted under 35 U.S.C. 154(b) by 48 days.

(21) Appl. No.: 12/196,129

(22) Filed: Aug. 21, 2008

(65) Prior Publication Data
US 2009/0155844 A1    Jun. 18, 2009

Related U.S. Application Data

(63) Continuation of application No. PCT/JP2007/053304, filed on Feb. 22, 2007.

(30) Foreign Application Priority Data

Feb. 22, 2006    (JP) ................... 2006-045788

(51) Int. Cl.
*C12P 21/00*    (2006.01)
*C07H 21/04*    (2006.01)
*C12N 5/10*    (2006.01)
(52) U.S. Cl. ............... 435/69.1; 435/325; 536/23.1
(58) Field of Classification Search ................. None
See application file for complete search history.

(56) References Cited

U.S. PATENT DOCUMENTS
2006/0234339 A1    10/2006    Yokoyama et al.

FOREIGN PATENT DOCUMENTS
WO    WO-2004/039989 A1    5/2004

OTHER PUBLICATIONS

Domitrovich et al Multiple, dispersed human U6 small nuclear RNA genes with varied transcriptional efficiencies. Nucleic acid research 2003, vol. 31, No. 9 see especially p. 2344.*
Takashi Kobayashi et al.RNA meeting (2005), vol. 7th, p. 101.*
Thompson et al (Strategies to express structural and catalytic RNAs in mammalian cells, Methods in Enzymology, vol. 306, pp. 241-260.*
Iives et al. Retroviral vectors designed for targetted expression of RNA polymerase III-driven transcripts:coparative study. Gene, 171 (1996) 203-208.*
Kohrer, C. et al., "Import of amber and ochre suppressor tRNAs into mammalian cells: a general approach to site-specific insertion of amino acid analouges into proteins", Proceedings of the National Academy of Sciences of USA, National Academy of Science, Washington, DC, US, vol. 98, No. 25, Dec. 4, 2001, pp. 14310-14315.
Murakawa, G. J. et al., "Expression of a transfer RNA gene in the context of the LAC-Z messenger RNA", Journal of Bacteriology, vol. 169, No. 2, 1987, pp. 546-552.
Polycarpo, Carla et al., "Activation of the 1-15 pyrrolysine suppressor tRNA requires formation of a ternary complex with class I and class II lysyl-tRNA synthetases", Molecular Cell, vol. 12, No. 2, Aug. 2003, pp. 287-284.
Takashi Kobayashi et al., RNA Meeting, vol. 7, pp. 101, 2005.
Blight, S.K. et al., Nature, vol. 431, pp. 333-335, 2004.
Domitrovich, A.M. et al., Nucleic Acids Res., vol. 31, No. 9, pp. 2344-2352, 2003.
Murphy, J.T. et al., J. Biol. Chem., vol. 262, No. 4, pp. 1795-1803, 1987.
Ilegems, E et al., Protein Eng. Des. Sel., vol. 17, No. 12, pp. 821-827, 2004.
Sakamoto, K. et al., Nucleic Acids Research vol. 30, No. 21, pp. 4692-4699, 2002.
Sprinzl, M. et al., "Compilation of tRNA sequences and sequences of tRNA genes" Nucleic Acids Research vol. 17, pp. 1-172 (1989).
Hirao, Ichiro et al., "An unnatural base pair for incorporating amino acid analogs into proteins" Nature Biotechnology vol. 20, pp. 177-182 (2002).
Hirao, Ichiro et al., "An unnatural hydrophobic base pair system: site-specific incorporation of nucleotide analogs into DNA and RNA" Nature Methods vol. 3 No. 9, pp. 729-735 (2006).

* cited by examiner

*Primary Examiner* — Kagnew H Gebreyesus
(74) *Attorney, Agent, or Firm* — Birch, Stewart, Kolasch & Birch, LLP

(57) ABSTRACT

There are provided a DNA construct comprising non-eukaryote-derived suppressor tRNA gene containing no internal promoter functioning in a eukaryotic cell, and a eukaryote-derived or bacteriophage-derived promoter linked at the 5' end of the tRNA gene, a method for synthesizing a suppressor tRNA by using the DNA construct, and a process for producing a non-natural amino acid-incorporated protein by using the same.

7 Claims, 9 Drawing Sheets

FIG. 1

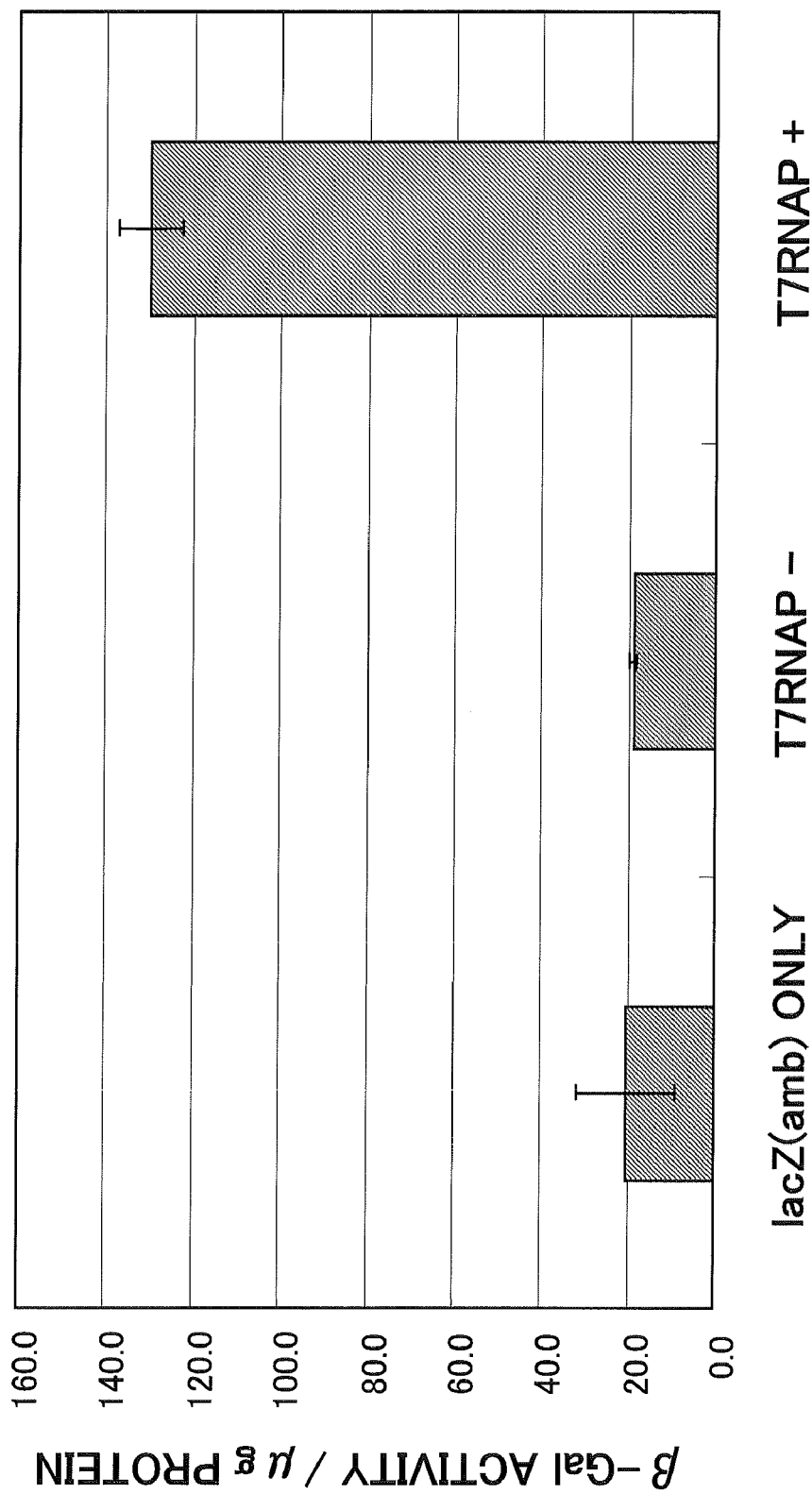

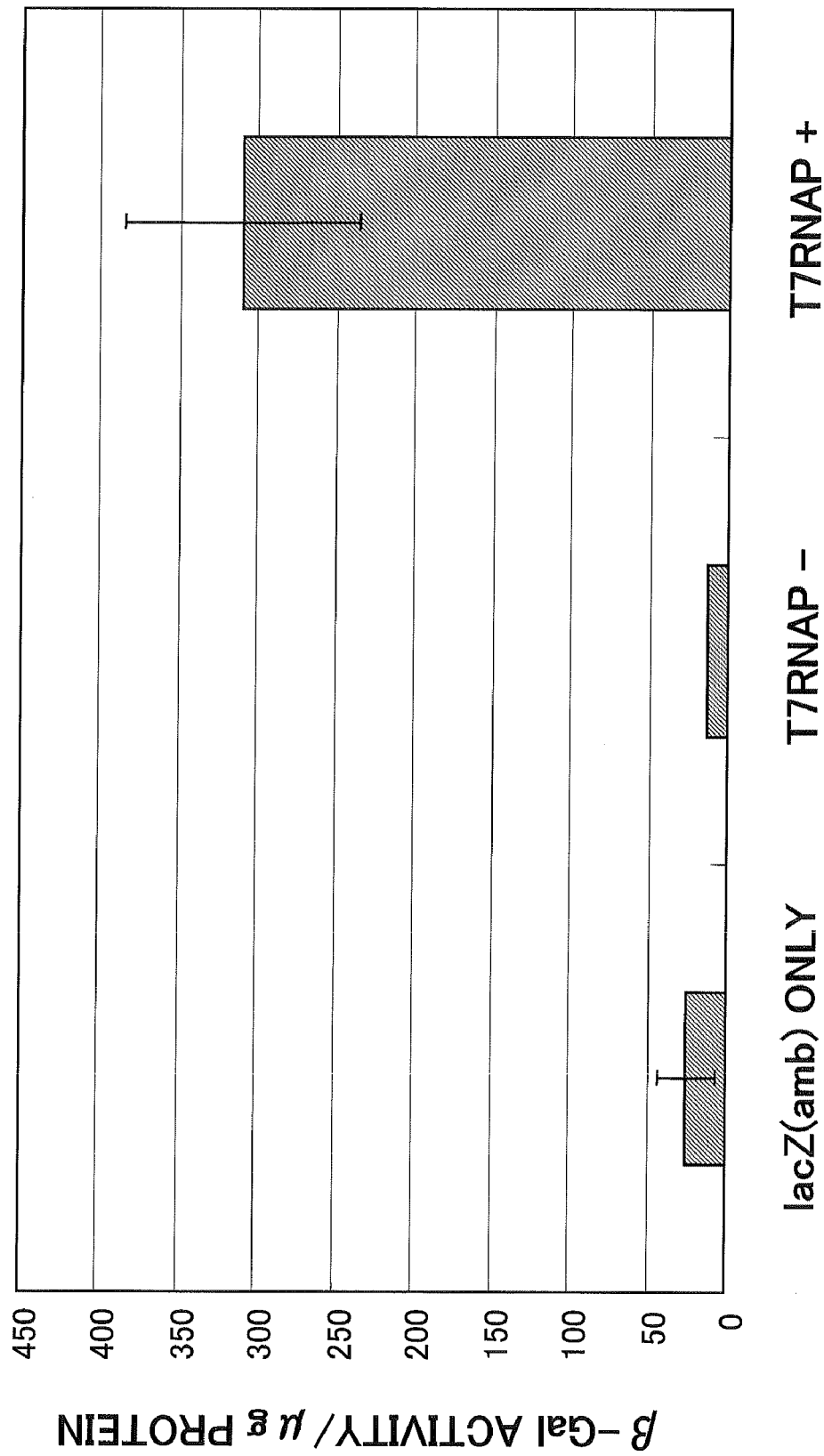

METHOD OF SYNTHESIZING A SUPPRESSOR TRNA, DNA CONSTRUCT AND USE THEREOF FOR PRODUCING A PROTEIN INCLUDING A NON-NATURAL AMINO ACID

RELATED APPLICATIONS

The present application is Continuation Application under 35 USC §120 of International Application No. PCT/JP2007/05334, filed on Feb. 22, 2007, which in turn claims priority under 35 USC §119 of Japanese Application No. 2006-045788, filed on Feb. 22, 2006.

TECHNICAL FIELD

The present invention relates to a method of synthesizing a tRNA and a DNA construct therefor, particularly to a method of synthesizing a suppressor tRNA corresponding to a non-natural amino acid and a DNA construct therefor, as well as a method of producing a protein incorporating a non-natural amino acid using the above.

BACKGROUND ART

A protein incorporating a non-natural amino acid (hereinafter also referred to as an "alloprotein") in which an amino acid residue at a desired position in a protein is replaced with an amino acid other than 20 different amino acids involved in normal protein synthesis (a non-natural amino acid) could offer an effective means of analyzing the function and structure of a protein. Meanwhile, lysine derivatives include amino acids, such as acetyl-lysine, methyl-lysine etc., which are synthesized by post-translational modification. Such amino acids are well-known particularly as those involved in regulation of gene expression by histones and are also known as those involved in regulation of transcriptional activation, regulation of protein-protein interaction, and suppression/promotion of ubiquitination for many types of proteins. It is expected that many findings concerning acetylation, methylation etc. of lysine could be made if those lysine derivatives could be introduced site-specifically into a protein synthesized by a eukaryote.

Pyrrolysyl tRNA synthetase (PylRS) is a novel aminoacyl tRNA synthetase (aaRS) found in a methanogenic archaebacterium (Methanosarcina). A corresponding tRNA (pyrrolysine tRNA) is a suppressor tRNA, which has a unique secondary structure such as an unusually small D loop, etc. Recently, it was found that in *Escherichia coli*, PylRS and pyrrolysine tRNA do not interact with endogenous aaRS and tRNA (orthogonality), and pyrrolysine could be introduced specifically into the site of an amber codon in a protein (Non-Patent Document 1). Further, it has been reported that a wild-type PylRS can bind a non-natural amino acid such as Nε-Boc-L-lysine to pyrrolysine tRNA in *Escherichia coli* (Non-Patent Document 1).

On the other hand, in a mammalian cell, enzymes that phosphorylate tyrosine residues in proteins (tyrosine kinases) play an important role in transducing extracellular signals, such as by growth stimulating factors, into the nucleus. The tyrosine kinases include one capable of phosphorylating a tyrosine derivative and one incapable of phosphorylating a tyrosine derivative. For example, it was shown that a Src kinase phosphorylates an iodotyrosine residue but an EGF receptor cannot do so. Thus, it is useful in examining interaction of a desired protein with various tyrosine kinases in a cell if an alloprotein, the desired protein into which a tyrosine derivative is incorporated, could be synthesized in a mammalian cell. For example, it is important in analysis of signal transduction mechanisms to examine which tyrosine kinase phosphorylates the desired protein. Further, these non-natural amino acid-incorporated proteins could be useful in themselves as material for analysis of the function and structure of a protein, and could have a novel bioactivity.

As an expression method of an alloprotein like the above in an animal cell, there has been developed a method of expressing in an animal cell (A) a mutant tyrosyl tRNA synthetase (hereinafter referred to as "mutant TyrRS"), which is a variant of a tyrosyl tRNA synthetase derived from *Escherichia coli* and has an increased specificity to a non-natural tyrosine derivative as compared with the specificity to a tyrosine, (B) a suppressor tRNA originating from *eubacterium*, such as *bacillus*, mycoplasma, and *staphylococcus*, and capable of binding to the above tyrosine derivative in the presencGe of the above mutant tyrosyl tRNA synthetase, and (C) a desired protein gene including a nonsense mutation or frame shift mutation at a desired position. The above tyrosine derivative has been incorporated into the position of the nonsense mutation or frame shift mutation of the above protein (Patent Document 1 and Non-Patent Document 2).

Hereupon, it is required that the above suppressor tRNA originating from the non-eukaryote is transcribed by an RNA polymerase in a eukaryotic cell. In contrast to one kind of RNA polymerase in prokaryotic cells, it is known that in eukaryotic cells, there are three different kind of RNA polymerases I, II, and III (polI, polII, and polIII) that share functions. PolI synthesizes ribosomal RNA, PolII synthesizes mRNA, and PolIII synthesizes 5S rRNA, tRNA, U6 small nuclear RNA (snRNA), etc. Therefore, tRNA in a eukaryotic cell is synthesized by transcription by RNA polymerase III. Genes transcribed by the RNA polymerase III are classified broadly into three groups according to characteristics of their promoter structures, the groups including, as their representative genes, a 5S rRNA gene (Type I promoter), a tRNA gene (Type II promoter), and a U6 small nuclear RNA gene (Type III promoter), respectively. The type II promoter, which transcribes a tRNA, is an internal promoter made up of two regions in a tRNA coding sequence, the consensus sequences of which are known as box A and box B. The consensus sequence of the box A consists of the positions 8-19: TRGCNNAGYNGG (SED ID NO:1), and the consensus sequence of the box B consists of the positions 52-62: GGT-TCGANTCC (SED ID NO:2). Accordingly, for example, the suppressor tyrosine tRNA of *Bacillus stearothermophilus*, although it originates from a prokaryote, can be expressed in an animal cell without any alterations, because of the presence of the box A and box B in its suppressor tyrosine tRNA coding sequence (refer to Non-patent Document 3, for example).

Here, incorporation of an amino acid into the position of the nonsense mutation in the above protein is referred to as suppression. Because there are only three different types of stop codons, a maximum of three types of non-natural amino acids can be incorporated into one type of protein. In vitro experiments have developed artificial base pairs in addition to naturally occurring base pairs (refer to Non-patent Documents 4 and 5), and an RNA containing artificial base pairs as mentioned above can be transcribed in vitro by using an RNA polymerase of T7 bacteriophage. It is expected that the following could be achieved: increase in the number of codon types, which are now $4^3$, by using artificial base pairs in codons encoding amino acids, and introduction of a plurality of non-natural amino acids into one type of protein by getting the codons that do not encode natural amino acids to encode non-natural amino acids.

[Patent Document 1] WO2004/039989A1
[Non-Patent Document 1] Blight, S. K. et al., Nature, 431, 333-335 (2004)
[Non-Patent Document 2] Sakamoto, K. et al., Nucleic Acids Research 30, 4692-4699 (2002)
[Non-Patent Document 3] M. Sprinzl et al., Nucleic Acids Research 17, 1-172 (1989)
[Non-Patent Document 4] Hirao, I. et al., Nature Biotechnology 20, 177-182 (2002)
[Non-Patent Document 5] Hirao, I. et al., Nature Methods 3, 729-735 (2006)

DISCLOSURE OF THE INVENTION

Problems to be Solved by the Invention

In the case of the above-mentioned expression of a suppressor tRNA originating from a non-eukaryote in a eukaryotic cell, however, the problem is raised that, if the tRNA has sequences significantly different from the consensus sequences of the eukaryote in place of box A and box B, the sequences do not function as an internal promoter, and only an extremely small amount of transcription is achieved in an eukaryotic cell or almost no transcription occurs therein. For example, the D loop of a pyrrolysine tRNA originating from methanogenic archaebacterium, which lacks several bases and is unusually small, does not function as internal promoter in a eukaryotic cell. Further, a suppressor tyrosine tRNA of *Escherichia coli* has the box B consensus sequence in its sequence but does not contain the box A consensus sequence. Introduction of the boxes A and B into those tRNAs results in loss of their functions as tRNA so that alloproteins with an incorporated lysine derivative or tyrosine derivative cannot be synthesized even if a pyrrolysine tRNA or an *E. coli* suppressor tyrosine tRNA including boxes A and B is used.

On the other hand, it is unknown whether or not those suppressor tRNAs having no internal promoter would function as tRNA in cases where the suppressor tRNAs are expressed using an external promoter in a eukaryotic cell. That is, although it is required that base modification and formation of 3-dimentional structure, etc. after transcription normally occur in order that a tRNA functions, it remains unknown where a tRNA transcribed by an external promoter other than a type II promoter would be localized in the cell, whether it would undergo post-transcriptional modification or not, and further whether it would present biological functions or not.

Means to Solve the Problems

After investigations and considerations, the inventors have found out that a pyrrolysine tRNA originating from methanogenic archaebacterium or a suppressor tyrosine tRNA of *Escherichia coli* can be efficiently expressed in an animal cell by binding to its 5' end a promoter sequence of a eukaryotic tRNA nucleotide sequence or U1 and U6 snRNA gene(s). Further, it has been found out that the tRNA can be efficiently expressed by binding a bacteriophage-originating promoter sequence to the 5' end of the tRNA gene and introducing the promoter together with a RNA polymerase capable of transcription into an animal cell. The present invention has been accomplished based on those findings.

In accord with a first aspect of the present invention, there is provided a DNA construct comprising a suppressor tRNA gene of a non-eukaryote and lacking an internal promoter sequence that functions in a eukaryotic cell, and a promoter of a eukaryote linked to the 5' end of the tRNA gene. It is preferred that the tRNA gene is a pyrrolysine tRNA gene originating from an archaebacteria and/or a suppressor tyrosine tRNA gene originating from *Escherichia coli*, and the DNA construct further comprises a transcription terminator sequence linked to the 3' end of said tRNA gene. In a further preferable exemplary embodiment, the promoter of a eukaryote is a nucleotide sequence that induces transcription by RNA polymerase II or III. The nucleotide sequence that induces the transcription by the RNA polymerase II is preferably a promoter of a U1 snRNA gene, for example. Also, it is particularly preferred that the nucleotide sequence that induces the transcription by the RNA polymerase III is a promoter of a eukaryotic tRNA gene such as a human valine tRNA nucleotide sequence, or a promoter of a U6 snRNA gene, for example.

In accord with a second aspect of the present invention, there is provided i) a method of synthesizing a suppressor tRNA comprising causing the DNA construct to undergo transcription in a eukaryotic cell; ii) a recombinant eukaryotic cell that is transformed or transfected by the DNA construct; and iii) a method of synthesizing an aminoacyl-tRNA, comprising expressing a tRNA transcribed by the DNA construct and an aminoacyl-tRNA synthetase corresponding to said tRNA.

In accord with a third aspect of the present invention, there is provided a process for producing a protein incorporating a non-natural amino acid comprising: expressing, in the presence of the non-natural amino acid in a eukaryotic cell, (a) an aminoacy-tRNA synthetase for the non-natural amino acid, (b) a tRNA which is capable of binding to the non-natural amino acid in the presence of the aminoacyl-tRNA synthetase, and which is transcribed from the DNA construct, and (c) a desired protein that has a nonsense mutation or frame shift mutation at a desired position.

In accord with a forth aspect of the present invention, there is provided a DNA construct comprising: a suppressor tRNA gene from a non-eukaryote lacking an internal promoter sequence that functions in a eukaryotic cell, and a promoter originating from a bacteriophage linked to the 5' end of the tRNA gene. It is preferred that the tRNA gene is a pyrrolysine tRNA gene originating from archaebacteria and/or a suppressor tyrosine tRNA gene originating from *Escherichia coli*. The DNA construct further comprises a transcription terminator sequence linked to the 3' end of the tRNA gene. The bacteriophage promoter is preferably, but not restricted to, a T7 promoter, T3 promoter, or SP6 promoter.

In accord with a fifth aspect of the present invention, there are provided a method of synthesizing a suppressor tRNA comprising causing a DNA construct to undergo transcription in a eukaryotic cell, the DNA construct comprising a suppressor tRNA gene of a non-eukaryote lacking an internal promoter sequence that functions in a eukaryotic cell, and a promoter originating from bacteriophage linked to the 5' end of said tRNA gene; and a recombinant eukaryotic cell being transformed or transfected by the DNA construct and a gene expressing an RNA polymerase corresponding to the bacteriophage promoter.

In accord with a sixth aspect of the present invention, there is provided a process for producing a protein including a non-natural amino acid comprising i) preparing a DNA construct comprising a suppressor tRNA gene of a non-eukaryote and lacking an internal promoter sequence that functions in a eukaryotic cell, and a promoter from a bacteriophage operably linked to the 5' terminal region of the tRNA gene, wherein the suppressor tRNA is capable of binding to the non-natural amino acid in the presence of an aminoacyl-tRNA synthetase for the non-natural amino acid; and ii) expressing, in the presence of the non-natural amino acid in a eukaryotic cell, (a) a tRNA transcribed from the DNA construct, (b) an aminoacyl-tRNA synthetase for the non-natural amino acid, and (c) a desired protein that has a nonsense mutation or frame shift mutation at a desired position. The tRNA gene is preferably, but not restricted to, a pyrrolysine tRNA gene originating from archaebacteria and/or a suppressor tyrosine tRNA gene originating from *Escherichia coli*. Further, it is preferable that the non-natural amino acid is, but not restricted to, a lysine derivative or a tyrosine derivative.

In accord with a seventh aspect of the present invention, there is provided a process for producing a protein including a non-natural amino acid comprising: preparing a DNA construct comprising a suppressor tRNA gene of a non-eukaryote lacking an internal promoter sequence that functions in a eukaryotic cell, and a bacteriophage promoter operably linked to the 5' terminal region of the tRNA gene, wherein the suppressor tRNA is capable of binding to the non-natural amino acid in the presence of an aminoacyl-tRNA synthetase for the non-natural amino acid; and expressing, in the presence of the DNA construct and the non-natural amino acid in a eukaryotic cell, (a) an RNA polymerase corresponding to the bacteriophage promoter, (b) an aminoacyl-tRNA synthetase for the non-natural amino acid, and (c) a desired protein that has a nonsense mutation or frame shift mutation at a desired position. The tRNA gene is preferably, but not restricted to, a pyrrolysine tRNA gene originating from archaebacteria and/or a suppressor tyrosine tRNA gene originating from *Escherichia coli*. Further, it is preferable that the non-natural amino acid is, but not restricted to, a lysine derivative or a tyrosine derivative Meritorious Effects of the Invention Using a process in the present invention allows a tRNA originating from a non-eukaryote and an aminoacyl-tRNA, to be efficiently expressed in a eukaryotic cell, and a non-eukaryotic suppressor tRNA containing no internal promoter sequences (box A, box B) that function in a eukaryotic cell to be expressed in a eukaryotic cell. It is expected that using the process of the present invention allows expression of aminoacyl-tRNA containing an artificial, non-natural base in a eukaryotic cell, and synthesis of an alloprotein containing 4 or more different types of non-natural amino acids.

Further, using a process in the present invention allows synthesis of an alloprotein, particularly in eukaryotes, into which there is incorporated a lysine derivative such as Nε-acetyl-lysine, Nε-trimethyl-lysine, Nε-t-butoxycarbonyl-lysine, Nε-2-methylamino-benzoyl-lysine containing a fluorescent group, etc., by using a wild-type aminoacyl-tRNA synthetase originating from archaebacteria.

BRIEF DESCRIPTION OF THE DRAWINGS

FIG. 1 shows a cloverleaf structure of a pyrrolysine tRNA.
FIG. 7 shows a result of suppression of lacZ (91 amber) in the case of tRNA$^{Pyl}$ being expressed by using a T7 promoter in Example 5. It is apparent therefrom that in the case of T7 RNA polymerase being expressed (T7RNAP+), β-galactosidase activity detected is significantly high as compared with the case when T7 RNA polymerase is not expressed (T7RNAP−), and the amber codon of a lacZ gene is suppressed.
FIG. 8 shows a result of suppression of lacZ (91 amber) in the case of tRNA$^{Tyr}$ being expressed by using T7 promoter in Example 5. It is apparent therefrom that in the case of T7 RNA polymerase being expressed (T7RNAP+), β-galactosidase activity detected is significantly high as compared with the case when T7 RNA polymerase is not expressed (T7RNAP−), and the amber codon of a lacZ gene is suppressed.

Figure 2:
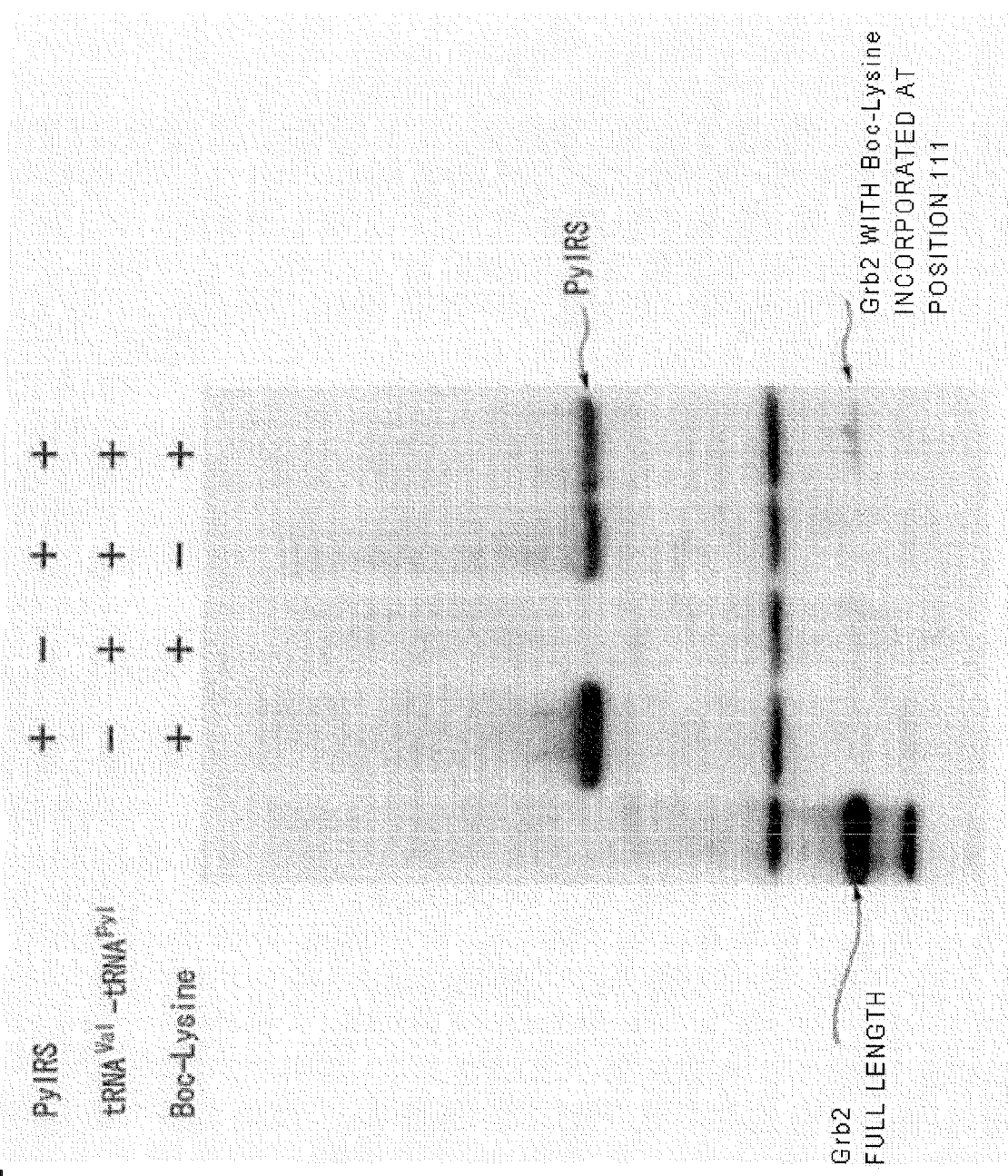
FIG. 2 shows a result of suppression of Grb2 (111amb) detected by western blot in Example 1.

PREFERRED MODES FOR CARRYING OUT THE INVENTION (Non-Natural Amino Acid)

A non-natural (non-naturally occurring) amino acid as may be used herein includes, for example, a lysine derivative or a tyrosine derivative. As a lysine derivative, a non-natural amino acid is preferably one in which the hydrogen atom bonded to the nitrogen atom at the ε position is replaced with another atom or chemical group. Lysine derivatives include pyrrolysine, Nε-t-butoxycarbonyl-lysine (Nε-Boc-lysine), Nε-acetyl-lysine, Nε-trimethyl-lysine, and Nε-2-methylamino-benzoyl-lysine (Nma-lysine), for example. Site-specific incorporation of methyllysine or acetyllysine, which are modified lysines present in a eukaryote, into a protein could produce many findings regarding methylation or acetylation of lysine. Such alloprotein with the lysine derivative incorporated is useful as material for analysis of function and structure of the protein, and could offer a target for drug development. Tyrosine derivatives include 3- or 4-substituted tyrosine made up of a tyrosine having a substituent at 3- or 4-position of the phenyl group thereof. 3-substituted tyrosine includes 3-halogenated tyrosine such as 3-iodotyrosine and 3-bromotyrosine. 4-substituted tyrosine includes 4-acetyl-L-phenylalanine, 4-benzoyl-L-phenylalanine, 4-azido-L-phenylalanine, O-methyl-L-tyrosine, 4-iodo-L-phenylalanine etc. Those amino acids can be prepared by known methods and are commercially available.

(Aminoacyl-tRNA Synthetase)

Aminoacyl-tRNA synthetase as used herein is tRNA synthetase capable of recognizing a non-natural amino acid and specifically recognizing a suppressor tRNA to produce a suppressor tRNA connected to such non-natural amino acid.

In a preferred exemplary embodiment, PylRS originating from a methanogenic archaebacterium is provided that is able to recognize, as an amino acid a lysine derivative and specifically recognize, as tRNA, a pyrrolysine tRNA (SEQ ID NO:4) used in combination to produce a suppressor tRNA connected to such lysine derivative. A methanogenic archaebacterium is preferably *Methanosarcina mazei* (*M. mazei*). PylRS is expressed in a eukaryotic cell, preferably in an animal cell, particularly preferably in a mammalian cell. In order to express PylRS in a cell, for example, a plasmid may be introduced into the mammalian cell which plasmid is constructed such that a DNA sequence made up of a wild-type gene originating in *Methanosarcina mazei*, added with FLAG tag etc. at its N terminal region, is amplified using PCR, followed by incorporation of the resultant DNA sequence into the NheI-BamHI site of commercially available pcDNA3.1 (Invitrogen), p. 107 (Cytotechnology, 3, 133 (1990)), p. 103 [J. Biochem. 101, 1307 (1987)] etc.

In other exemplary embodiments, there can be used various variants of TyrRS originating in *Escherichia coli* and capable of specifically recognizing a tyrosine derivative to produce a suppressor tRNA (SEQ ID NO:5) connected with the tyrosine derivative. For example, the *E. coli* TyrRS variant (V37C195) specifically recognizes 3-iodotyrosine. Alternatively, it has been reported that a TyrRS variant made up of *E. coli* TyrRS with five amino acid mutations introduced at positions 37, 126, 182, 185 and 186 recognized non-natural amino acids such as 4-azido-L-phenylalanine and 4-benzoyl-L-phenylalanine, etc. (Chin, J. W. Et al., Science, 301, 964-967, 2003). Wild-type *E. coli* TyrRS does not react with tRNA$^{Tyr}$ of eukaryotes, and tRNA$^{Tyr}$ of prokaryotes does not react with TyrRS of eukaryotes.

(tRNA)

It is required for tRNA used in combination with the above aminoacyl-tRNA synthetase to satisfy the requirements 1) that it is assigned to a nonsense codon other than codons assigned to usual 20 different amino acids, 2) that it is recognized only by the above non-natural amino acid-specific aminoacyl-tRNA synthetase but not recognized by an aminoacyl-tRNA synthetase normally present in a host cell (orthogonal tRNA) and 3) that is can be expressed in a eukaryotic cell. In a case where the aminoacyl-tRNA synthetase is PylRS, the corresponding pyrrolysine tRNA is a tRNA originating in a non-eukaryotic cell that has an anti-codon complementary to a nonsense codon and a 3-dimensional structure for functioning as suppressor tRNA, and it is expressed in a eukaryotic cell. That is, in this case, the tRNA is a suppressor tRNA that satisfies the requirement that it is assigned to a nonsense codon other than codons assigned to usual 20 different amino acids, and recognized only by the above lysine derivative-specific PylRS but not recognized by an aaRS normally present in a host cell (orthogonality); and is expressed in an animal cell.

Here, nonsense codons include UAG (amber), UAA (ochre), UGA (opal) etc., but UAG (amber) is preferably used. Instead of a nonsense codon, a codon made up of 4 or more bases (preferably 4 or 5 bases) (hereinafter referred to as a "frame shift codon") may be used.

Figure 1:
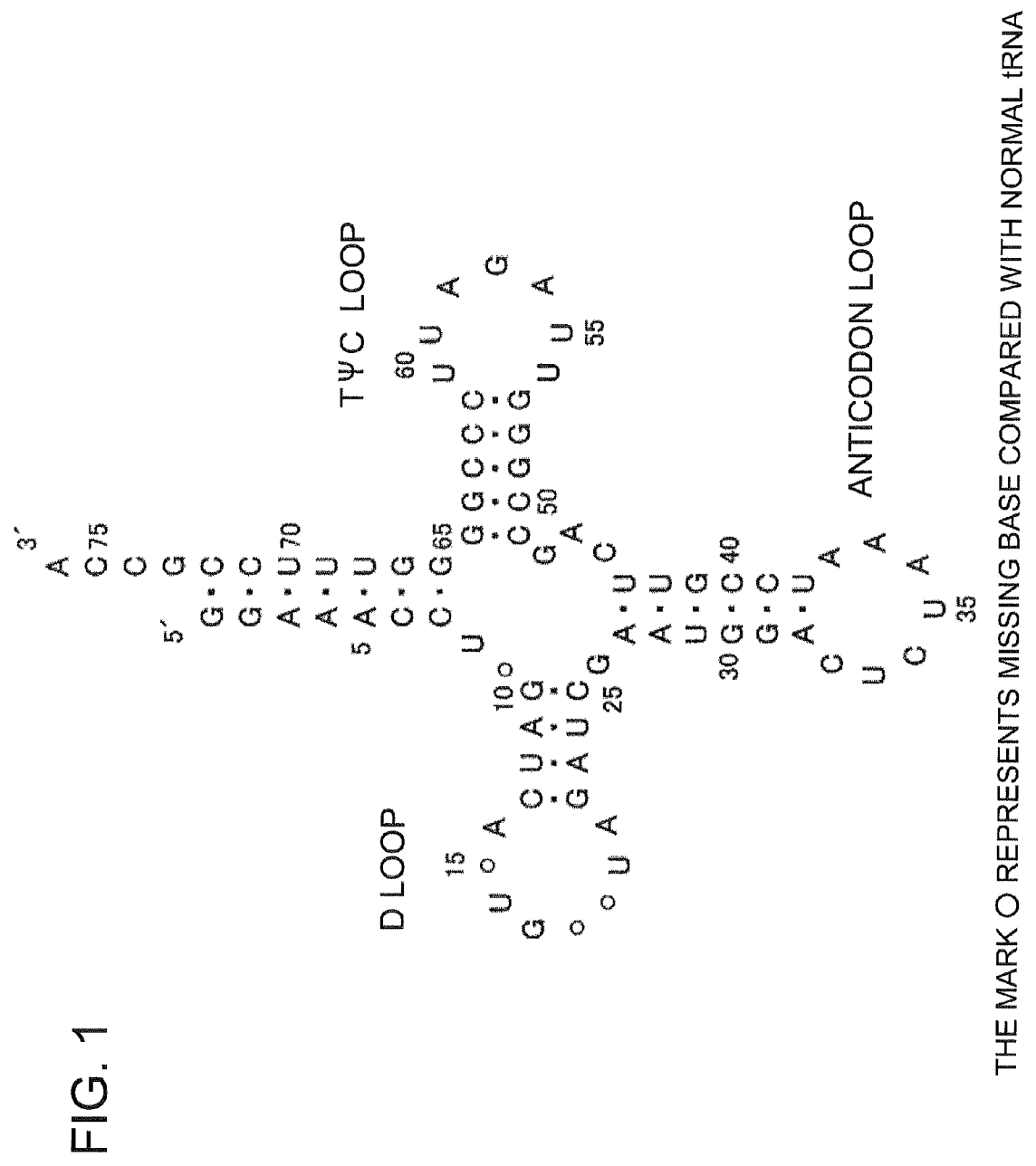

As mentioned above, expression of tRNA in a eukaryotic cell requires two internal promoters in a tRNA coding sequence, the consensus sequences of which are known as box A and box B. FIG. 1 shows a cloverleaf structure of a pyrrolysine tRNA. In FIG. 1, the mark ○ in the loop at the left (D loop) indicates lack of a base. As shown in FIG. 1, the pyrrolysine tRNA lacks 3 bases in the D loop and is extraordinarily small as compared with the D loops of the other tRNAs. In order to express the pyrrolysine tRNA in an animal cell, the box A and B sequences were incorporated into the pyrrolysine tRNA, but this resulted in a drastic change in the structure of the tRNA because of the anomalously small size of the D loop, and in a failure in retaining its suppressor activity.

(Synthesis of tRNA, Aminoacyl-tRNA)

In a method of synthesizing aminoacyl-tRNA according to the present invention, a tRNA of a non-eukaryote containing no internal promoter sequence that functions in a eukaryotic cell, a eukaryote-originating promoter being linked to the 5' end of the tRNA, is caused to undergo transcription in a eukaryotic cell, preferably in an animal cell, particularly preferably in a mammalian cell, which contains an aminoacyl-tRNA synthetase. In this case, it is preferable that a transcription terminator sequence is linked to the 3' end of the tRNA. To be more specific, an aminoacyl-tRNA of the present invention is obtained in the following manner: the sequence of a wild-type pyrrolysine tRNA of *Methanosarcina mazei* was synthesized from DNA primers, the 5' end of which is linked to a eukaryotic promoter and the 3' end of which is linked to a transcription terminator sequence, and this construct is incorporated into, for example, pcDNA3.1 or pCR4Blunt-TOPO (both available from Invitrogen). The resulting plasmid is introduced into an animal cell to express the tRNA, followed by transcription and processing in the animal cell.

As the above eukaryote-derived promoter, there can be used a nucleotide sequence that induces transcription by an RNA polymerase II or III. The nucleotide sequence that induces transcription by an RNA polymerase II is preferably a U1 snRNA gene promoter. However, it has been reported that a U6 snRNA gene promoter with mutated TATA box region acts as promoter of the U1 snRNA gene and thus such promoter may be used. The promoter nucleotide sequence that induces transcription by an RNA polymerase III is preferably a eukaryotic tRNA gene or U6 snRNA gene promoter. In this case, it is preferred that the eukaryotic tRNA gene is linked via a linker to the 5' end of a wild-type pyrrolysine tRNA gene. The linker includes, but is not restricted to, a linker cleaved by BglII, XbaI, XhoI etc. The tRNA gene linked to the 5' end is one originating from a eukaryote, which includes, but is not restricted to, an animal, a plant, an insect, etc. Among these, a human tRNA gene is preferable. An amino acid to which the tRNA should be linked may be any one of the usual 20 different naturally-occurring amino acids, preferably valine among them.

Human U6 small nuclear RNA (snRNA) is an RNA species which is abundantly present in a spliceosome that is formed at the stage of splicing by pre-mRNA and reaches $4-5 \times 10^5$ copies per cell. The U6 promoter is believed to drive transcription of a small heterologous RNA, the activity of the transcription being higher than the activity of transcription using a tRNA promoter. Although the U6 promoter and the tRNA promoter are both transcribed by PolIII, both are different from each other in location: i.e., the U6 promoter is located at 5' upstream of the structural gene whereas the tRNA promoter is located in the interior of its own structural gene. The human U6 snRNA promoter has distinctive promoter elements known as an enhancer region (or distal promoter region) and a core region (or proximal promoter region), and is preferably a nucleotide sequence, which is formed of the nucleotide sequence set forth in SEQ ID NO:3 or a nucleotide sequence being at least 30%, 50%, 70%, 80%, 90% or 95% homologous to the nucleotide sequence set forth in SEQ ID NO:3, and which has the activity of transcription by an RNA polymerase III in a mammalian cell. The degree of homology between nucleotide sequences can be represented by percentage of identity of two appropriately aligned nucleotide sequences, which means incidence of accurately identical amino acids between the sequences. Appropriate alignment between sequences for identity comparison may be determined using, for example, the BLAST algorithm (Altschul S F J Mol Biol 1990 Oct. 5; 215(3):403-10).

In the present invention the above tRNA can be efficiently transcribed in a eukaryotic cell also by using a promoter originating from bacteriophage. To be specific, possible bacteriophage promoters include, but are not restricted to, a T7 promoter, T3 promoter and SP6 promoter originating from bacteriophage of *Escherichia coli*. These promoters may be inserted into any positions within the 5' terminal region of the above tRNA gene, but the insertion position is preferably 10-50 bp upstream from the transcription initiation site of the gene. In the case of a bacteriophage promoter being used, it is required to use a eukaryotic cell in which a bacteriophage RNA polymerase corresponding to such promoter is expressed. To be specific, T7 RNA polymerase, T3 RNA polymerase, and SP6 RNA polymerase may be used with the above promoters. It has been reported that when expressed in a mammalian cell, T7 RNA polymerase caused transcription of RNA from DNA containing a T7 promoter sequence, and the amount of the transcribed RNA reached a maximum of 20% of the total RNAs in the cell. It has been reported that, as in the case of a T7 RNA polymerase, a T3 RNA polymerase and a SP6 RNA polymerase have been used, the promoters thereof being as short as 20 bp or less like the T7 promoter, and the RNA polymerases each having substantially the same ability of RNA transcription (as the T7 RNA polymerase) to prepare a large amount of RNA in a mammalian cell. The T7 promoter of the nucleotide sequence set forth in SEQ ID NO:13, or a sequence formed of a nucleotide sequence being at least 70%, 80%, 90% or 95% homologous to the nucleotide sequence set forth in SEQ ID NO:13 and being capable of inducing transcription by a T7 RNA polymerase in a mammalian cell is preferred as a bacteriophage promoter.

(Protein into which a Non-Natural Amino Acid is Incorporated)

In the present invention, proteins into which a non-natural amino acid is incorporated are not restricted to particular types. Such proteins may be any proteins capable of expression and further can be heterologous recombinant proteins. Types of the proteins include, for example, so-called signaling related proteins, receptors, growth factors, cell cycle related factors, transcription factors, translation factors, transport related proteins, secretory proteins, cytoskeletal proteins, enzymes, chaperones, or disease related proteins, where the diseases include cancers, diabetes or genetic disease etc.

In the present invention, it is required to introduce a nonsense codon (an amber codon in the case of a suppressor tRNA being an amber suppressor) or a frame shift codon into a site into which a non-natural amino acid, in particular a lysine derivative or a tyrosine derivative, is to be incorporated, whereby a non-natural amino acid, in particular a lysine derivative, can be specifically incorporated into the nonsense codon (amber codon) site or the frame shift codon site. As used herein, a "frame shift mutation" is a mutation in an amino acid sequence that shifts the frame to be translated that is caused by deletion or insertion of 1, 2, or 4 bases, and the aberrant codon formed at the mutated site is referred to as a "frame shift codon". Preferably, a frame shift codon is a codon formed of 4 or 5 bases. It has been tried to extend the genetic code by using 4-base codons in various host cells. In the case of *Escherichia coli*, for example, the 4-base codon of AGGA is an alternative codon that is usable without causing much disturbance of cell function (Anderson, J. C. et al., Proc. Natl. Acad. Sci., USA 101, 7566-7571).

Methods for performing site-specific mutagenesis of a protein may be any well-known methods, and are not restricted to a particular one. For example, such mutagenesis may be conducted as required according to a method described in Gene 152, 271-275 (1995); Methods Enzymol. 100, 468-500 (1983); Nucleic Acids Res.12, 9441-9456 (1984); Proc. Natl. Acad. Sci. USA 82, 488-492 (1985) or "Saiboukougaku bessatsu 'Sinsaiboukougakujikken protocol', Shyujyunshya, 241-248 (1993)", or a method using "QuickChange Site-Directed Mutagenesis Kit" (Stratagene)

In the present invention, expression can be performed in an animal cell, and thus a non-natural amino acid can be incorporated into such protein that is not or is poorly expressed in *Escherichia coli* or a cell-free protein system or that cannot undergo post-translational modification necessary for changing to an active form. Various types of such proteins are known to a person of ordinary skill in the art. For example, there may be synthesized an alloprotein of, but not restricted to, a tyrosine kinase type receptor such as human EGFR, etc. (Cell, 110, 775-787 (2002)), human Groucho/TLE1 protein (Structure 10, 751-761 (2002)) or rat muscle-specific kinase (Structure 10, 1187-1196 (2002)).

In the method of the present invention, an alloprotein is expressed in an animal cell so that a non-natural amino acid, in particular a lysine derivative, can be incorporated into a carbohydrate chain-linked glycoprotein. Particularly, in the case of a type of glycoprotein whose pattern of addition of carbohydrate chain in a cell-free protein system is different from its original (natural) pattern, a system in an animal cell of the present invention is thought to be an effective measure to obtain an alloprotein to which is added a glycoprotein of a pattern of interest (an original pattern).

A protein for incorporation of a non-natural amino acid, in particular a lysine derivative, may be expressed, for example, as follows: a gene having a sequence constructed such that its codon corresponding to the position of a desired amino acid of a desired protein is replaced with a nonsense codon or a frame shift codon and a desired tag is added to the C terminus thereof is integrated into the BamHI-XhoI site of pcDNA4/TO etc. to produce a plasmid, which is introduced into an animal cell, resulting in expression thereof.

(Host)

An animal cell as host (cell) used in the present invention is preferably a mammalian cell in which a recombinant gene system is established. Examples of useful mammalian host cell systems include a Chinese hamster ovary (CHO) cell and a COS cell. More unique examples include the SV40-transformed simian kidney CV1 system (COS-7, ATCC CRL 1651); human embryo kidney system (293 cell or subcloned 293 cell for growth in suspension culture, J. Gen Virol., 36:59 (1977)); Chinese hamster ovary cell/-DHFR (CHO, Proc. Natl. Acad. Sci. USA, 77:4216 (1980)); mouse Sertoli's cell (TM4, Biol. Reprod., 23:243-251 (1980)); human lung cell (W138, ATCC CCL 75); human liver cell (Hep G2, HB 8065); and mouse breast cancer cell (MMT 060562, ATCC CCL51). An expression system for each of those host cells is established, and it is within the technical skill of a person of ordinary skill in the art to select an appropriate host cell.

Methods for introducing a vector into the above host cells include, for example, electroporation (Nucleic, Acids Res. 15, 1311-1326 (1987)), a calcium phosphate method (Mol. Cell. Biol. 7, 2745-2752 (1987)), a lipofection method (Cell 7, 1025-1037 (1994); Lamb, Nature Genetics 5, 22-30 (1993)), etc. These methods may be conducted, for example, in accord with a method described in Molecular Cloning 3$^{rd}$ edition, Cold Spring Harbor Laboratory Press (2001) etc. In accord with one exemplary embodiment of the present invention, there is provided a recombinant eukaryotic cell, preferably a recombinant mammalian cell, transformed or transfected with an expression vector of the above non-eukaryotic suppressor tRNA.

(Method for Producing a Protein with Incorporated Non-Natural Amino Acid)

As an example, expression of an alloprotein with an incorporated lysine derivative is explained below. An animal cell is incubated under appropriate conditions in a culture medium suitable for the growth of the animal cell (for example, Opti-MEMI (Gibco BRL) etc. in the case of a CHO cell), the animal cell containing (A) an expression vector expressing an aminoacyl-tRNA synthetase, in particular a PylRS, in the animal cell; (B) an expression vector expressing in the animal cell a *Methanosarcina mazei* pyrrolysine tRNA capable of binding to a non-natural amino acid, in particular a lysine derivative, in the presence of the above aminoacyl-tRNA synthetase (in particular PylRS); (C) an expression vector expressing a desired protein subjected to nonsense mutation or frame shift mutation at a desired position; and a non-natural amino acid, in particular a lysine derivative. In the case of a CHO cell, for example, the cell is incubated at ca. 37 degrees Celsius for ca. 24 hours.

Alternatively, in the case of the above pyrrolysine tRNA expressed by using a bacteriophage promoter, it is preferable to introduce, in addition to the above (A) to (C), (D) a vector expressing in an animal cell an RNA polymerase gene capable of transcription of the above bacteriophage promoter. For example, as RNA polymerases for transcription of the above T7 promoter, T3 promoter, and SP6 promoter, there are known a T7 RNA polymerase, a T3 RNA polymerase, and SP6 RNA polymerase, respectively.

Some examples of the present invention are detailed below but it should be understood that the present invention is not restricted to the examples mentioned below.

EXAMPLES

In these examples, there were conducted experiments for incorporation of a lysine derivative or a tyrosine derivative into position 111 of human Grb2 and position 91 of β-galactosidase. In this regard, the Grb2 is a protein involved in cancer by interaction with an epidermal growth factor receptor in a cell.

(Construction of PylRS and TyrRS Expression Plasmids)

A PylRS expression plasmid was constructed by PCR amplifying a DNA sequence (SEQ ID NO:8) made up of a wild type PylRS gene of *Methanosarcina mazei*, the N terminus region of which was linked to a FLAG tag. and incorporated into the NheI-BamHI site of pcDNA3.1 to generate the expression plasmid.

On the other hand, the expression plasmid PEYSM1 of 3-iodo-L-tyrosine specific mutant of *Escherichia coli* tyrosyl tRNA synthetase ((TyrRS V37C195, supra., Non-Patent Document 2) has been reported. Transfection into a mammalian culture cell of this plasmid together with an expression plasmid of a suppressor tRNA followed by addition of 3-iodo-L-tyrosine to a cell culture medium allows incorporation of the 3-iodo-L-tyrosine into the amber codon site of a protein gene with an amber mutation. The method of preparing the above expression plasmid is described in the above Patent Document 1 and Non-Patent Document 2, the contents of both documents being incorporated herein by reference. In addition, there has been reported mutant(s) specific to 4-azido-L-phenylalanine and 4-benzoyl-L-phenylalanine (Chin et al., supra). Those mutant TyrRSs were cloned into the multiple cloning site of pcDNA4/TO.

(Construction of Suppressor tRNA Expression Plasmid)

A sequence (SEQ ID NO: 11) was synthesized from a DNA primer. This sequence was made up of a wild type *M. mazei* pyrrolysine tRNA gene linked at the 5' end to a human valine tRNA gene via a linker (SEQ ID NO:10) and a leader, and further linked at the 3' end to a transcription termination sequence. This sequence was introduced into pCR4Blunt-TOPO, resulting in construction of a tRNA$^{VAL}$-tRNA$^{Pyl}$ tandem expression plasmid. A tRNA$^{VAL}$-tRNA$^{Tyr}$ tandem expression plasmid was constructed in a similar manner for expression of *Escherichia coli* suppressor tRNA$^{Tyr}$.

A tRNA expression plasmid with a U6 promoter was constructed by the following method. PCR was performed with a pcDNA3.1 vector template, using a primer made up of a CMV enhancer region to which a EcoRI site was added at the 5' side and to which a portion of the 5' side sequence of a U6 promoter was added at the 3' side. And PCR was performed with a siSTRIKE template, using a primer made up of a U6 promoter region having a portion of the 3' end sequence of a CMV enhancer at the 5' side and an XbaI site added to the 3' side. The two different PCR amplification fragments were joined to each other by overlap PCR to produce a DNA fragment having the structure—EcoRI site/CMV enhancer/U6 promoter/XbaI site. The so-produced fragment was treated with EcoRI and XbaI and then cloned into pUC119.

The above prepared plasmid was treated with XbaI and HindIII. The resulting product was joined to a fragment containing a tRNA$^{Pyl}$-terminator isolated from the previously prepared tRNA$^{VAL}$-tRNA$^{Pyl}$ tandem expression plasmid by XbaI and HindIII digestion, as a result of which there was obtained an expression plasmid having a DNA fragment of a nucleotide sequence set forth in SEQ ID NO:6. A plasmid made up of pcDNA3.1+Zeo having three tandem tRNA$^{Pyl}$ linked to the multiple cloning site was constructed as a control.

Likewise, a similar expression plasmid, but using *Escherichia coli* suppressor tyrosine tRNA instead of *Methanosarcina mazei* wild type pyrrolysine tRNA$^{Pyl}$, having the CMV enhancer and promoter of human U6 snRNA was constructed in a similar manner (SEQ ID NO:7). Here, it has been reported that the CMV enhancer activates RNA transcription from U6 promoter.

(Construction of Reporter Gene Expression Plasmid)

Using a QUICK CHANGE site-directed mutagenesis kit (Stratagene), the leucine codon at position 111 of human grb2 was converted to an amber codon (grb2 (111 amber)). Subsequently, a gene (SEQ ID NO:12) constructed such that a FLAG tag (DYKDDDDK, amino acids 217-224 in SEQ ID NO:12) was added to the C terminus thereof was incorporated into the BamHI-XhoI site of pcDNA4/TO to produce a plasmid for detection of suppression.

Likewise, a tyrosine codon at position 91 of *Escherichia coli* β-galactosidase (lacZ) was converted to an amber codon (lacZ (91 amber)) and cloned into the multiple cloning site of pcDNA3.1+ (Zeo resistant).

Introduction of Gene into Cell and Suppression Reaction

Example 1

Grb2 Amber Suppression by tRNA$^{Pyl}$ Linked to Human Valine tRNA Gene Promoter Chinese hamster ovary cells (CHO cells) cultivated in a 2.0 ml culture scale 6-well plate (as subculture medium, DMEM/F-12 (Gibco), 10% FBS (ICN), 1/100 penicillin-streptomycin (Gibco) were used) were provided with 0.5 μg/well of three different expression plasmids: PylRS, tRNA$^{Pyl}$ linked to a human valine tRNA gene promoter, and grb2 (111 amber) in various combinations thereof (see RESULT), and transfection was conducted under 90% confluent state. The transfection was performed using Lipofectamine 2000 (Invitrogen)

according to the instruction manual from Invitrogen. Opti-MEM (Gibco) was used as the culture medium for the transfection. The transfected cell culture medium (solution) was replaced with DMEM/F-12 (Gibco) in the presence or absence of 1 mM Nε-Boc-lysine (Bachem), expression of the plasmid genes was induced by addition of 1 µg/mL tetracycline, and incubation was conducted at 37 degrees Celsius for ca. 20 hours in a $CO_2$ incubator.

The above cultured cells from which the cell culture medium (solution) was removed were washed with buffer solution, followed by lysis of the cells to recover proteins. SDS-polyacrylamide gel electrophoresis was performed to separate the proteins from each other according to molecular weights thereof, followed by electroblotting (100 V, 1 hour) to membrane. Anti-FLAG M2 (Sigma) was used as primary antibody for detection of grb2 (111 amber) expression product, and sheep whole antibody conjugated with horseradish peroxidase for anti-mouse IgG (Amersham) was used as secondary antibody. As a detection reagent, ECL western blotting detection reagent (Amersham) was used. Measurement was conducted using a cooled CCD camera LAS 1000 plus (Fuji Film).

FIG. 2 shows a result detected by western blotting of suppression of Grb2 (111amb). Lane 1 on the left is a control for showing the position of the band of full-length Grb2. Wild type Grb2 has FLAG tag added to the C terminus thereof, and the band thereof is detected at the position indicated by the arrow for Grb2 in cases where it is synthesized to the C terminus thereof. Lanes 2 to 4 show results in the case of lack of any one of PylRS, pyrrolysine tRNA and Nε-Boc-lysine. In these cases, a full-length Grb2 was not synthesized. Contrary, lane 5 shows a result in the case of all of PylRS, pyrrolysine tRNA and Nε-Boc-lysine being introduced into a cell, wherein the full-length Grb2 was synthesized. It is apparent from the results that by PylRS and pyrrolysine tRNA, Nε-Boc-lysine was incorporated into an amber codon incorporated into position 111 of Grb2.

Example 2

Grb2 Amber Suppression by $tRNA^{Tyr}$ and $tRNA^{Pyl}$ Linked to U6 Promoter

Figure 3:
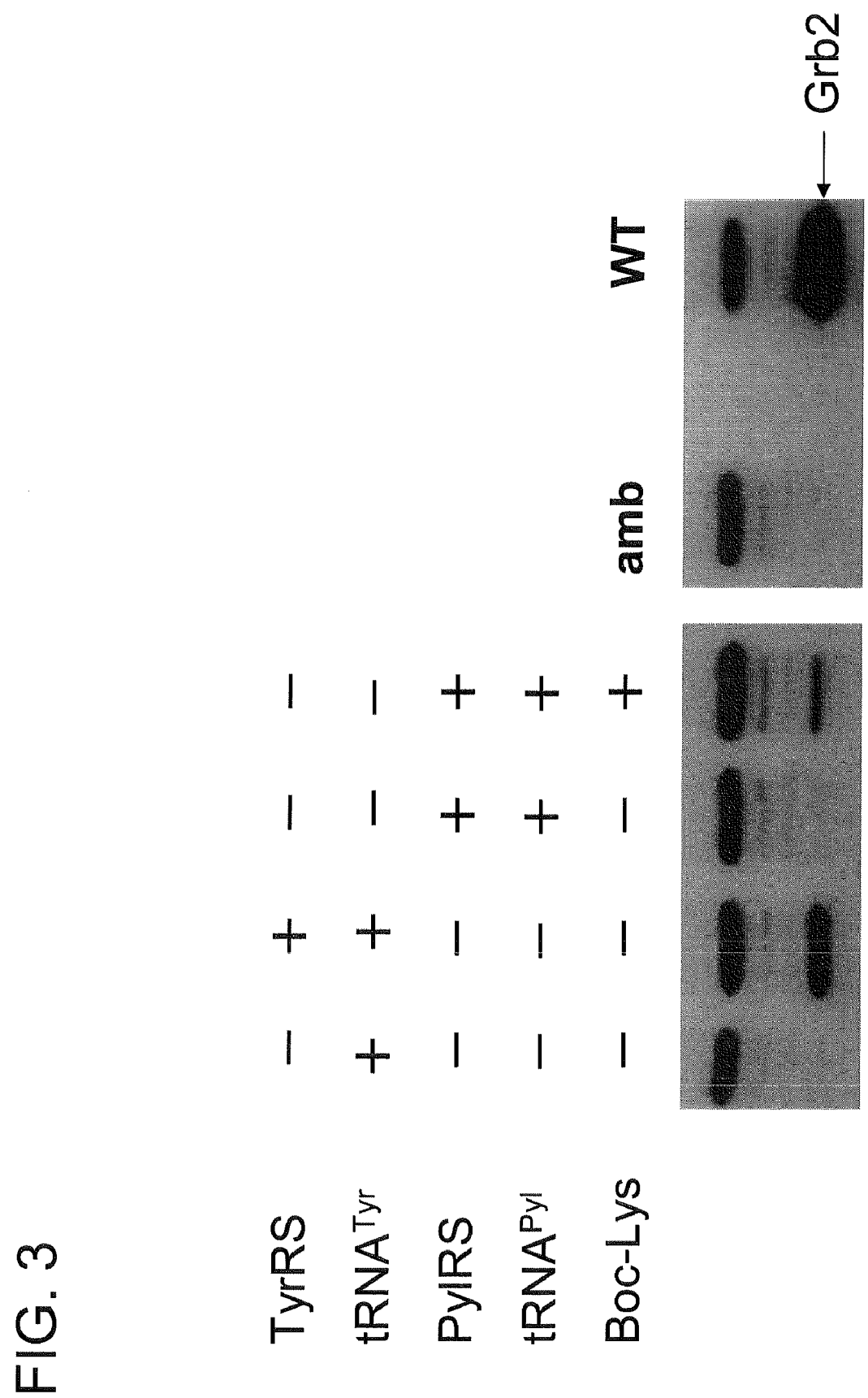
FIG. 3 shows a result of suppression of Grb2 (111amb) detected by western blot in Example 2.

Subsequently, human Grb2 gene, wild type TyrRS, and PylRS, which were prepared using a similar method in the above Example, were expressed and were subjected to suppression by *Methanosarcina mazei* wild type pyrrolysine $tRNA^{Pyl}$ having U6 promoter or *Escherichia coli* suppressor $tRNA^{Tyr}$. FIG. 3 shows a result detected by western blotting of suppression of Grb2 (111amb). Lane on the most right is a control for showing the position of bands of wild type Grb2. Two lanes on the left show results in cases where *Escherichia coli* suppressor $tRNA^{Tyr}$ having U6 promoter was expressed. From the band of Grb2 having been detected depending on expression of TryRS, it is apparent that tyrosine was incorporated into the amber codon of Grb2. Two lanes in the middle show results in cases where pyrrolysine $tRNA^{Pyl}$ having U6 promoter was expressed. From the band of Grb2 having been detected by addition of Nε-Boc-lysine to the culture medium, it is apparent that Nε-Boc-lysine was incorporated into the amber codon of Grb2. The results revealed that the tRNA gene having a U6 promoter linked to its 5' end was transcribed in a mammalian cell. A control experiment in which tyrosine is not added to the culture medium in the case of tyrosine tRNA being expressed was not conducted because cells do not grow in the absence of tyrosine.

Example 3 lacZ Amber Suppression by $tRNA^{Pyl}$

Chinese hamster ovary cells (CHO-TRex cells) were seeded in a 24-well plate at $1.2 \times 10^5$ cells/well and incubated in DMEM/F-12 culture media (Gibco) containing 10% fetal bovine serum (ICN) and 1/100 penicillin-streptomycin (Gibco). The next day, when the culture was 95% confluent, transfection was conducted by using 0.4 µg lacZ (91 amber), 0.2 µg PylRS expression plasmids, and three different suppressor $tRNA^{Pyl}$ expression plasmids (each containing human valine tRNA, U6 promoter, and CMV enhancer) prepared in the above Example. The transfection was conducted using 2 µl Lipofectamine 2000 (Invitrogen) according to the instruction manual therefor. Opti-MEM (Gibco) was used as culture medium for the transfection.

Figure 4:
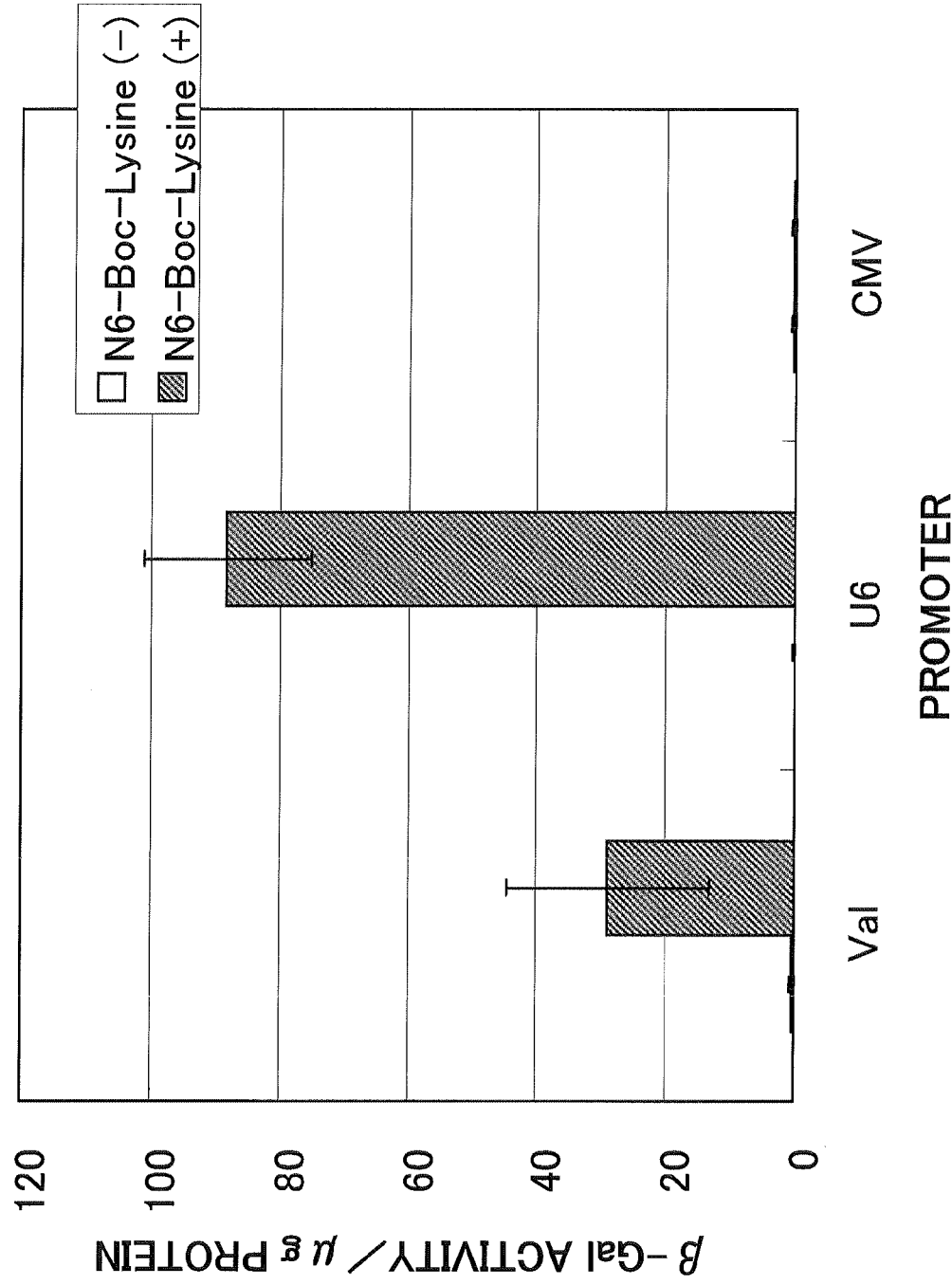
FIG. 4 shows a result of lacZ amber suppression in the case of tRNA$^{Pyl}$ being expressed by using 3 different promoters or enhancers.

The transducted cell culture medium was replaced with DMEM/F-12 (Gibco) in the presence or absence of 1 mM Boc-lysine (Bachem), expression was induced by addition of 1 µg/mL tetracycline, and incubation was conducted at 37 degrees Celsius for ca. 20 hours in a $CO_2$ incubator. The next day, proteins were recovered from the cells, and lacZ enzyme activities thereof were examined using a β-Gal reporter assay kit (TOYOBO). The result is shown in FIG. 4. It is apparent therefrom that in cases where either human valine tRNA promoter or U6 promoter was used, β-galactosidase activity was detected by addition of Boc-lysine to the medium, and thus the amber codon of lacZ gene was suppressed. On the contrary, in the case of the tRNA expression vector using a CMV promoter but not containing the human valine tRNA promoter or U6 promoter, suppression was not caused because β-galactosidase activity was not detected regardless of whether Boc-lysine was added or not. It is assumed that expression of suppressor tRNA by U6 promoter is significantly high as compared with that by human valine tRNA promoter.

Example 4 lacZ Amber Suppression by $tRNA^{Tyr}$ linked to U6 Promoter

Figure 5:
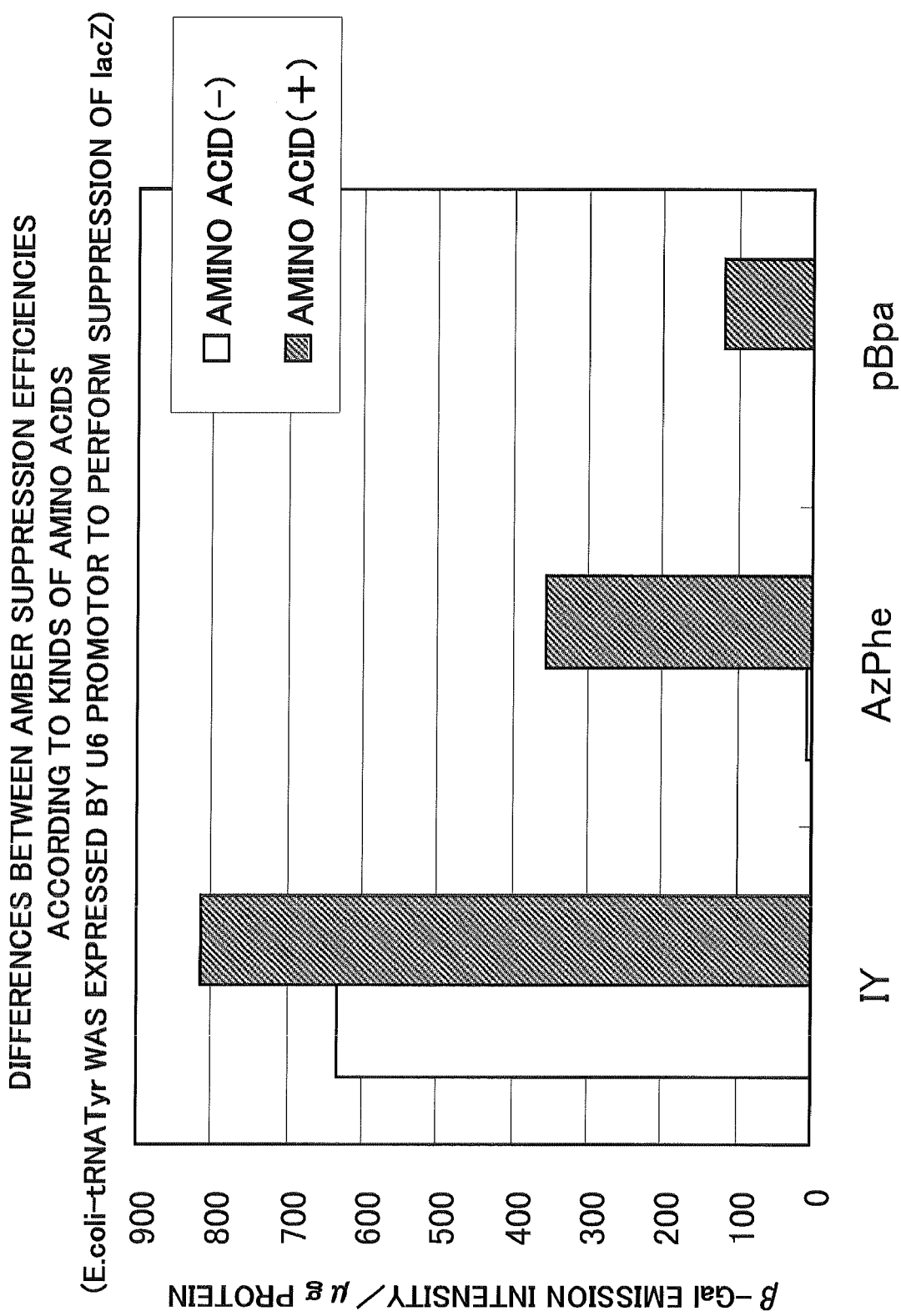
FIG. 5 shows a result of lacZ amber suppression by tRNA$^{Tyr}$ linked to a U6 promoter in cases where 3 different non-natural amino acids were added.

By a method similar to that of Example 3, a U6 promoter-linked *Escherichia coli* suppressor $tRNA^{Tyr}$ gene and three different mutant TyrRS expression plasmids were expressed, and lacZ amber suppression was performed by addition to the culture of three types of tyrosine derivatives; iodotyrosine (IY), azidophenylalanine (AzPhe) and parabenzoylphenylalanine (pBpa). The result is shown in FIG. 5. It is apparent therefrom that in each case where any one of the amino acids was added, significantly high β-galactosidase activity was detected as compared with the case where no amino acids were added, and thus the amber codon of lacZ gene was suppressed. In this regard, it seems that the detection of β-galactosidase activity even in the absence of iodotyrosine is due to the suppression caused even in the case of no addition of IY by IY-specific mutant TyrRS, which incorporates not only iodotyrosine but also tyrosine.

Reference Example 1

Figure 6:
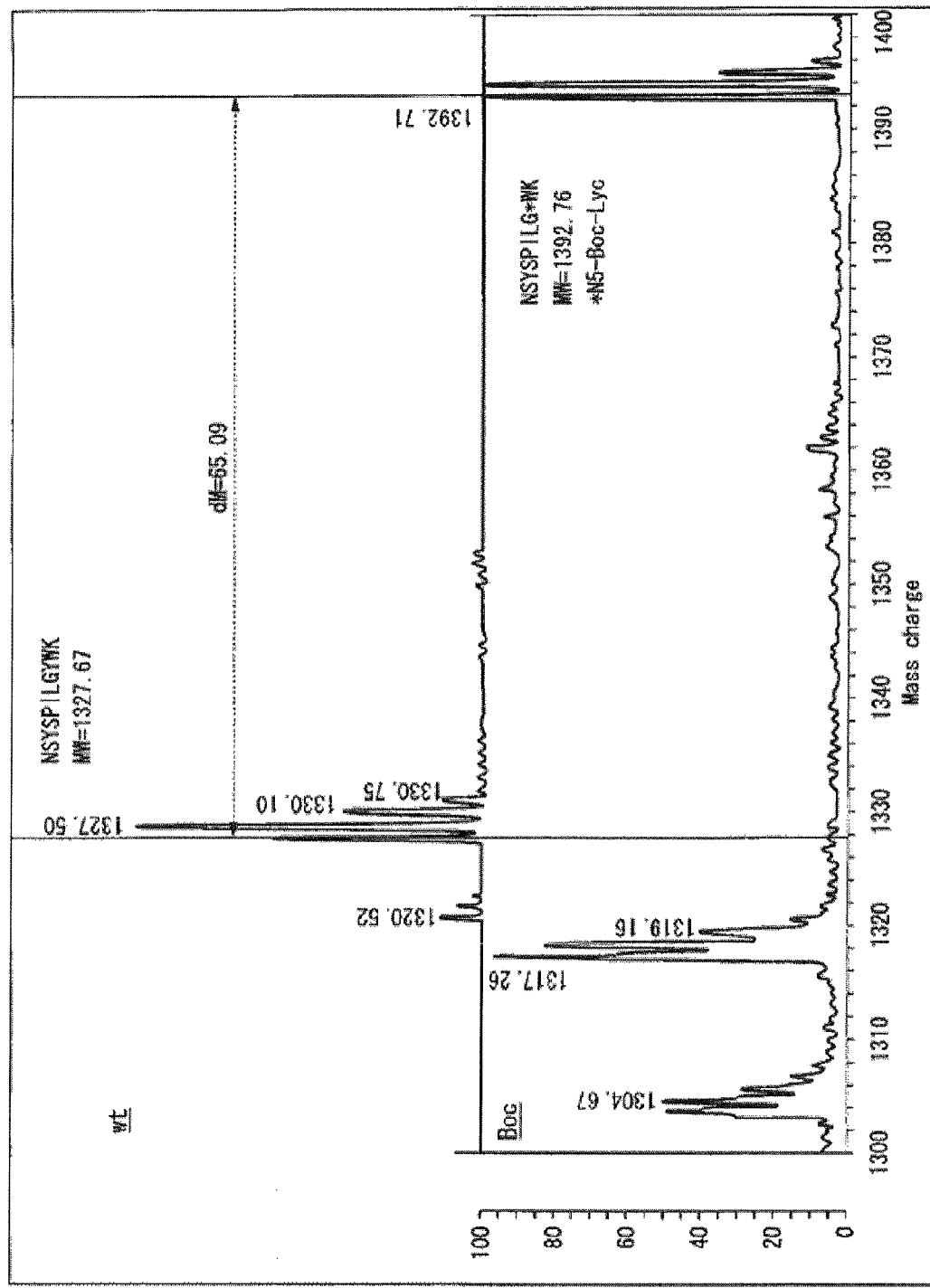
FIG. 6 shows mass spectrum data demonstrating that in *Escherichia coli*, Nε-Boc-lysine was incorporated into a peptide in the presence of PylRS and pyrrolysine tRNA.

FIG. 6 shows data of mass spectrometry indicating that in *Escherichia coli*, Nε-Boc-lysine was incorporated into a peptide in the presence of PylRS and pyrrolysine tRNA. As shown in FIG. 6, the peak of molecular weight (MW) 1327.67 indicates a peptide whose sequence is NSYSPILGYWK. The peak of molecular weight 1392.76 indicates a peptide whose tyrosine presented at the 9th position from the left was replaced with Nε-Boc-lysine (which is indicated with the mark "*").

Example 5

Construction of Expression System of Suppressor tRNA by T7 Promoter, and lacZ Amber Suppression A T7 RNA polymerase gene was amplified by PCR and cloned between the EcoRI and XhoI sites of pcDNA4/TO to produce a T7 RNA polymerase expression plasmid. In order to produce a T7-tRNA$^{Tyr}$ gene, first PCR was performed using U6-tRNA$^{Tyr}$ (SEQ ID NO:7) as template, thereby adding a T7 promoter to the tRNA$^{Tyr}$ sequence, to be cloned into pCR4blunt-TOPO. Then, the T7-tRNA$^{Tyr}$ gene was cut out by treatment with EcoRI, to be cloned into EcoRI site of pBR322. The so prepared T7-tRNA$^{Tyr}$ gene and a portion of the plasmid sequence (SEQ ID NO:15) were amplified by PCR, and the DNA obtained was purified and used to transform cells. In order to construct a tRNA$^{Pyl}$ expression plasmid, the pBR322 into which T7-tRNA$^{Tyr}$ gene was cloned as mentioned above was treated with XbaI and HindIII, followed by isolation of a fragment containing the tRNA$^{Pyl}$-terminator from the tRNA expression plasmid with U6 promoter by means of XbaI and HindIII digestions, to couple them with each other. The so prepared T7-tRNA$^{Pyl}$ gene and a portion of a plasmid sequence (SEQ ID NO:14) were amplified by PCR, and the DNA obtained was purified and used to transform cells.

Using a method similar to that of Example 3, transfection was performed by using 0.2 μg T7-tRNA$^{Pyl}$ expression plasmid, 0.1 μg PylRS expression plasmid, 0.4 μg lacZ (91 amber) expression plasmid, and 0.3 μg T7 RNA polymerase expression plasmid to conduct lacZ amber suppression, except that incubation was conducted in DMEM/F-12 culture medium (Gibco) without 1/100 penicillin-streptomycin (Gibco). The result is shown in FIG. 7. It is apparent therefrom that in the case where T7 RNA polymerase was expressed (T7RNAP+), significantly high β-galactosidase activity was detected as compared with the case where T7 RNA polymerase was not expressed (T7RNAP−), and thus the amber codon of lacZ gene was suppressed.

Using a method similar to that of Example 3, transfection was performed by using 0.18 μg T7-tRNA$^{Tyr}$ gene DNA, 0.1 μg TyrRS expression plasmid, 0.4 μg lacZ (91 amber) expression plasmid, and 0.3 μg T7 RNA polymerase expression plasmid to conduct lacZ amber suppression. However, incubation was conducted in DMEM/F-12 culture medium (Gibco) without 1/100 penicillin-streptomycin (Gibco). The result is shown in FIG. 8. It is apparent therefrom that in the case where T7 RNA polymerase was expressed, significantly high β-galactosidase activity was detected as compared with the case where T7 RNA polymerase was not expressed, and thus the amber codon of lacZ gene was suppressed.

Example 6

Construction of Expression System of Suppressor tRNA by U1 snRNA-Type Transcription Promoter, and lacZ Amber Suppression Construction of tRNA expression plasmid by U1snRNA type-promoter was conducted according to the following method. Using the previously prepared U6-tRNA$^{Tyr}$ (SEQ ID NO:7) as template, the region from 198 bases upstream of the U6 promoter transcription initiation site to upstream of the TATA box was amplified by using the following primers:

```
5'-ATGATATCAGAGGGCCTATTTCCCAT-3'      (SEQ ID NO: 16)
5'-TGCTCGAGAAGCCAAGAATCGAAATAC-       (SEQ ID NO: 17)
3'.
```

This region includes a transcription element PSE, wherein the amplified DNA fragment has an EcoRV site added at its 5' end and an XhoI site added at its 3' end. The PCR product was integrated into the EcoRV-XhoI site of plasmid pcDNA3.1+. Vector-originating EcoO109I and NotI sites are present downstream of the XhoI site. A sequence downstream of the TATA box of the U6 promoter and a terminator for stopping transcription by polymerase III were inserted between the XhoI and EcoO109I sites. After insertion of the tRNA$^{Tyr}$ sequence into the EcoO109I site, a 3' box, which is a terminator of polymerase II, was further inserted into the NotI site. The whole region from EcoRV through the 3' box constitutes a PSE-tRNA$^{Tyr}$ gene (SEQ ID NO:18). This gene was amplified by PCR and cloned into pCR4blunt-TOPO to produce a plasmid, which corresponds to the PSE-tRNA$^{Tyr}$ expression plasmid. The so prepared PSE-tRNA$^{Tyr}$ gene has a U6 promoter from which the TATA sequence is removed so that transcription by RNA polymerase II is caused (Das et al., Nature 1995, Vol. 374, pp. 657-660). In addition, PCR amplification was performed using the following two primers having CMV enhancers similar to those of the U6 promoter:

```
                                      (SEQ ID NO: 19)
  5'-ATCGAATTCTAGTTATTAATAGTAATCAATTACG-3'
and (SEQ ID NO: 20)
  5'-AGCCTTGTATCGTATATGC-3',
``` and 5' phosphorylation was further conducted, followed by insertion into the EcoRI site of the PSE-tRNA$^{Tyr}$ gene to produce CMV-DSE-PSE-tRNA$^{Tyr}$.

Figure 9A:
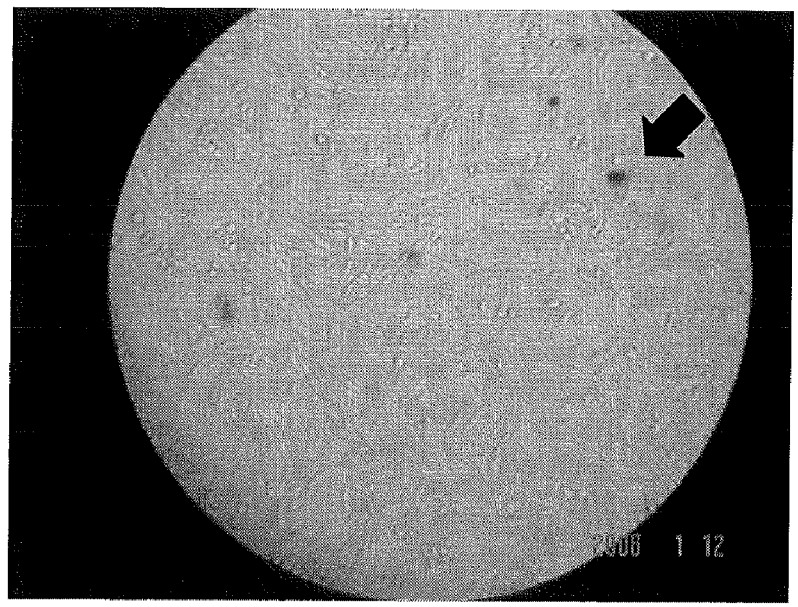
FIG. 9 shows a result of suppression of lacZ (91 amber) detected by cellular staining in the case of tRNA$^{Tyl}$ being expressed by using a U1 snRNA transcription promoter in Example 6.
Figure 9B:
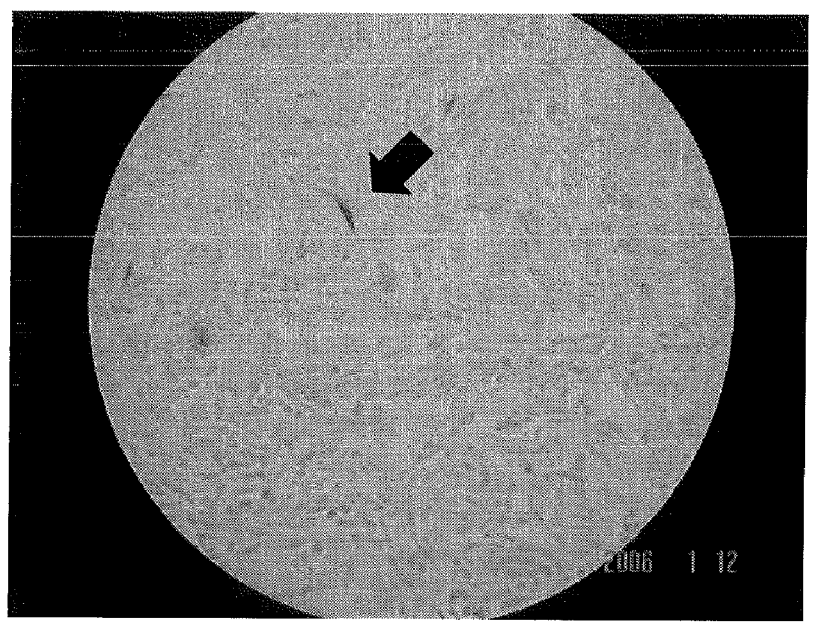

Using a method similar to that of Example 3, transfection was conducted by using 0.2 μg of PSE-tRNA$^{Tyr}$ expression plasmid or CMV-PSE-tRNA$^{Tyr}$ expression plasmid, 0.2 μg of TyrRS expression plasmid, and 0.4 μg of lacZ (91 amber) expression plasmid. On the day following the transfection, cells were stained using a β-Galactosidase Staining Kit (Mirus) to examine whether amber suppression of lacZ was caused. A cell having caused suppression is expected to be stained blue. FIG. 9 shows photographs depicting results of staining cells, wherein stained cells are indicated with arrows. Presence or absence of the enhancer did not cause a particularly large difference. The suppression activities, even though low, were confirmed in both cases.

INDUSTRIAL APPLICABILITY

The present invention is able to effectively produce alloprotein(s) into which there is incorporated a non-natural amino acid such as a lysine derivative, a tyrosine derivative, etc.

The invention claimed is:

1. A DNA construct comprising a suppressor tRNA gene from a non-eukaryotic origin, wherein said tRNA gene contains no internal promoter sequence, has a eukaryotic promoter linked to the 5' end of said tRNA gene, and functions in a eukaryotic cell, wherein said tRNA gene is a tRNA gene from an archaebacteria and said eukaryotic promoter is a pol III type III promoter.

2. The DNA construct of claim 1, wherein said tRNA gene is a pyrrolysine tRNA gene from archaebacteria origin.

3. The DNA construct of claim 1, further comprising a transcription terminator sequence linked to the 3' end of said tRNA gene.

4. The DNA construct of claim 1, wherein said pol III type III promoter is a promoter of a U6 snRNA gene.

5. The DNA construct of claim 4, wherein said promoter of the U6 snRNA gene has the nucleotide sequence set forth in SEQ ID NO: 3 or a nucleotide sequence that is at least 90% identical thereto, and induces transcription by RNA polymerase III in a mammalian cell.

6. A method of synthesizing a suppressor tRNA comprising expressing the DNA construct of claim 1 in a eukaryotic cell.

7. A recombinant eukaryotic cell that is transformed or transfected by the DNA construct of claim 1.

* * * * *

SEQUENCE LISTING

<160> NUMBER OF SEQ ID NOS: 20

<210> SEQ ID NO 1
<211> LENGTH: 12
<212> TYPE: DNA
<213> ORGANISM: Artificial Sequence
<220> FEATURE:
<221> NAME/KEY: misc_signal
<223> OTHER INFORMATION: consensus sequence of Type II promoter
<220> FEATURE:
<221> NAME/KEY: misc_feature
<222> LOCATION: (5)..(6)
<223> OTHER INFORMATION: n stands for any base
<220> FEATURE:
<221> NAME/KEY: misc_feature
<222> LOCATION: (10)..(10)
<223> OTHER INFORMATION: n stands for any base

<400> SEQUENCE: 1
trgcnnagyn gg                                                          12

<210> SEQ ID NO 2
<211> LENGTH: 11
<212> TYPE: DNA
<213> ORGANISM: Artificial Sequence
<220> FEATURE:
<221> NAME/KEY: misc_signal
<223> OTHER INFORMATION: consensus sequence of Type II promoter
<220> FEATURE:
<221> NAME/KEY: misc_feature
<222> LOCATION: (8)..(8)
<223> OTHER INFORMATION: n stands for any base

<400> SEQUENCE: 2
ggttcgantc c                                                           11

<210> SEQ ID NO 3
<211> LENGTH: 250
<212> TYPE: DNA
<213> ORGANISM: Artificial Sequence
<220> FEATURE:
<223> OTHER INFORMATION: Human U6 snRNA promoter

<400> SEQUENCE: 3
agagggccta tttcccatga ttccttcata tttgcatata cgatacaagg ctgttagaga      60
gataattaga attaatttga ctgtaaacac aaagatatta gtacaaaata cgtgacgtag     120
aaagtaataa tttcttgggt agtttgcagt tttaaaatta tgttttaaaa tggactatca     180
tatgcttacc gtaacttgaa agtatttcga tttcttggct ttatatatct tgtggaaagg     240
acgaaacacc                                                            250

<210> SEQ ID NO 4
<211> LENGTH: 72
<212> TYPE: RNA
<213> ORGANISM: Methanosarcina mazeii

<400> SEQUENCE: 4
ggaaaccuga ucauguagau cgaauggacu cuaaauccgu ucagccgggu uagauucccg      60
ggguuuccgc ca                                                          72

<210> SEQ ID NO 5
<211> LENGTH: 85
<212> TYPE: RNA
<213> ORGANISM: Escherichia coli

<400> SEQUENCE: 5

```
gguggguuc ccgagcggcc aaagggagca gacucuaaau cugccgucau cgacuucgaa      60
gguucgaauc cuuccccac cacca                                            85
```

<210> SEQ ID NO 6
<211> LENGTH: 852
<212> TYPE: DNA
<213> ORGANISM: Artificial Sequence
<220> FEATURE:
<223> OTHER INFORMATION: U6-tRNAPyl expression construct

<400> SEQUENCE: 6

```
tagttattaa tagtaatcaa ttacggggtc attagttcat agcccatata tggagttccg      60
cgttacataa cttacggtaa atggcccgcc tggctgaccg cccaacgacc cccgcccatt     120
gacgtcaata atgacgtatg ttcccatagt aacgccaata gggactttcc attgacgtca     180
atgggtggag tatttacggt aaactgccca cttggcagta catcaagtgt atcatatgcc     240
aagtacgccc cctattgacg tcaatgacgg taaatggccc gcctggcatt atgcccagta     300
catgacctta tgggactttc ctacttggca gtacatctac gtattagtca tcgctattac     360
catggtgatg cggttttggc agtacatcaa tgggcgtgga tagcggtttg actcacgggg     420
atttccaagt ctccacccca ttgacgtcaa tgggagtttg ttttggcacc aaaatcaacg     480
ggacagaggg cctatttccc atgattcctt catatttgca tatacgatac aaggctgtta     540
gagagataat tagaattaat ttgactgtaa acacaaagat attagtacaa atacgtgac      600 gtagaaagta ataatttctt gggtagtttg cagttttaaa attatgtttt aaaatggact     660
atcatatgct taccgtaact tgaaagtatt tcgatttctt ggctttatat atcttgtgga     720
aaggacgaaa caccgagatc ttctagactc gagggaaacc tgatcatgta gatcgaatgg     780
actctaaatc cgttcagccg ggttagattc ccggggtttc cggacaagtg cggtttttt      840 ctccagctcc cg                                                         852
```

<210> SEQ ID NO 7
<211> LENGTH: 865
<212> TYPE: DNA
<213> ORGANISM: Artificial Sequence
<220> FEATURE:
<223> OTHER INFORMATION: U6-tRNATyr expression construct

<400> SEQUENCE: 7

```
tagttattaa tagtaatcaa ttacggggtc attagttcat agcccatata tggagttccg      60
cgttacataa cttacggtaa atggcccgcc tggctgaccg cccaacgacc cccgcccatt     120
gacgtcaata atgacgtatg ttcccatagt aacgccaata gggactttcc attgacgtca     180
atgggtggag tatttacggt aaactgccca cttggcagta catcaagtgt atcatatgcc     240
aagtacgccc cctattgacg tcaatgacgg taaatggccc gcctggcatt atgcccagta     300
catgacctta tgggactttc ctacttggca gtacatctac gtattagtca tcgctattac     360
catggtgatg cggttttggc agtacatcaa tgggcgtgga tagcggtttg actcacgggg     420
atttccaagt ctccacccca ttgacgtcaa tgggagtttg ttttggcacc aaaatcaacg     480
ggacagaggg cctatttccc atgattcctt catatttgca tatacgatac aaggctgtta     540
gagagataat tagaattaat ttgactgtaa acacaaagat attagtacaa atacgtgac      600 gtagaaagta ataatttctt gggtagtttg cagttttaaa attatgtttt aaaatggact     660
atcatatgct taccgtaact tgaaagtatt tcgatttctt ggctttatat atcttgtgga     720
```

```
aaggacgaaa caccgagatc ttctagactc gagggtgggg ttcccgagcg gccaaaggga      780
gcagactcta aatctgccgt catcgacttc gaaggttcga atccttcccc caccagacaa      840
gtgcggtttt tttctccagc tcccg                                            865

<210> SEQ ID NO 8
<211> LENGTH: 1392
<212> TYPE: DNA
<213> ORGANISM: Methanosarcina mazeii
<220> FEATURE:
<221> NAME/KEY: CDS
<222> LOCATION: (1)..(1392)
<223> OTHER INFORMATION:
<220> FEATURE:
<221> NAME/KEY: misc_feature
<222> LOCATION: (1)..(27)
<223> OTHER INFORMATION: FLAG tag

<400> SEQUENCE: 8 atg gac tac aag gac gac gat gac aag atg gat aaa aaa cca cta aac         48
Met Asp Tyr Lys Asp Asp Asp Asp Lys Met Asp Lys Lys Pro Leu Asn
1               5                   10                  15 act ctg ata tct gca acc ggg ctc tgg atg tcc agg acc gga aca att         96
Thr Leu Ile Ser Ala Thr Gly Leu Trp Met Ser Arg Thr Gly Thr Ile
            20                  25                  30 cat aaa ata aaa cac cac gaa gtc tct cga agc aaa atc tat att gaa        144
His Lys Ile Lys His His Glu Val Ser Arg Ser Lys Ile Tyr Ile Glu
        35                  40                  45 atg gca tgc gga gac cac ctt gtt gta aac aac tcc agg agc agc agg        192
Met Ala Cys Gly Asp His Leu Val Val Asn Asn Ser Arg Ser Ser Arg
    50                  55                  60 act gca aga gcg ctc agg cac cac aaa tac agg aag acc tgc aaa cgc        240
Thr Ala Arg Ala Leu Arg His His Lys Tyr Arg Lys Thr Cys Lys Arg
65                  70                  75                  80 tgc agg gtt tcg gat gag gat ctc aat aag ttc ctc aca aag gca aac        288
Cys Arg Val Ser Asp Glu Asp Leu Asn Lys Phe Leu Thr Lys Ala Asn
                85                  90                  95 gaa gac cag aca agc gta aaa gtc aag gtc gtt tct gcc cct acc aga        336
Glu Asp Gln Thr Ser Val Lys Val Lys Val Val Ser Ala Pro Thr Arg
            100                 105                 110 acg aaa aag gca atg cca aaa tcc gtt gcg aga gcc ccg aaa cct ctt        384
Thr Lys Lys Ala Met Pro Lys Ser Val Ala Arg Ala Pro Lys Pro Leu
        115                 120                 125 gag aat aca gaa gcg gca cag gct caa cct tct gga tct aaa ttt tca        432
Glu Asn Thr Glu Ala Ala Gln Ala Gln Pro Ser Gly Ser Lys Phe Ser
    130                 135                 140 cct gcg ata ccg gtt tcc acc caa gag tca gtt tct gtc ccg gca tct        480
Pro Ala Ile Pro Val Ser Thr Gln Glu Ser Val Ser Val Pro Ala Ser
145                 150                 155                 160 gtt tca aca tca ata tca agc att tct aca gga gca act gca tcc gca        528
Val Ser Thr Ser Ile Ser Ser Ile Ser Thr Gly Ala Thr Ala Ser Ala
                165                 170                 175 ctg gta aaa ggg aat acg aac ccc att aca tcc atg tct gcc cct gtt        576
Leu Val Lys Gly Asn Thr Asn Pro Ile Thr Ser Met Ser Ala Pro Val
            180                 185                 190 cag gca agt gcc ccc gca ctt acg aag agc cag act gac agg ctt gaa        624
Gln Ala Ser Ala Pro Ala Leu Thr Lys Ser Gln Thr Asp Arg Leu Glu
        195                 200                 205 gtc ctg tta aac cca aaa gat gag att tcc ctg aat tcc ggc aag cct        672
Val Leu Leu Asn Pro Lys Asp Glu Ile Ser Leu Asn Ser Gly Lys Pro
    210                 215                 220 ttc agg gag ctt gag tcc gaa ttg ctc tct cgc aga aaa aaa gac ctg        720
Phe Arg Glu Leu Glu Ser Glu Leu Leu Ser Arg Arg Lys Lys Asp Leu
```

```
                  225                 230                 235                 240 cag cag atc tac gcg gaa gaa agg gag aat tat ctg ggg aaa ctc gag       768
Gln Gln Ile Tyr Ala Glu Glu Arg Glu Asn Tyr Leu Gly Lys Leu Glu
                245                 250                 255 cgt gaa att acc agg ttc ttt gtg gac agg ggt ttt ctg gaa ata aaa       816
Arg Glu Ile Thr Arg Phe Phe Val Asp Arg Gly Phe Leu Glu Ile Lys
                260                 265                 270 tcc ccg atc ctg atc cct ctt gag tat atc gaa agg atg ggc att gat       864
Ser Pro Ile Leu Ile Pro Leu Glu Tyr Ile Glu Arg Met Gly Ile Asp
                275                 280                 285 aat gat acc gaa ctt tca aaa cag atc ttc agg gtt gac aag aac ttc       912
Asn Asp Thr Glu Leu Ser Lys Gln Ile Phe Arg Val Asp Lys Asn Phe
                290                 295                 300 tgc ctg aga ccc atg ctt gct cca aac ctt tac aac tac ctg cgc aag       960
Cys Leu Arg Pro Met Leu Ala Pro Asn Leu Tyr Asn Tyr Leu Arg Lys
305                 310                 315                 320 ctt gac agg gcc ctg cct gat cca ata aaa att ttt gaa ata ggc cca      1008
Leu Asp Arg Ala Leu Pro Asp Pro Ile Lys Ile Phe Glu Ile Gly Pro
                325                 330                 335 tgc tac aga aaa gag tcc gac ggc aaa gaa cac ctc gaa gag ttt acc      1056
Cys Tyr Arg Lys Glu Ser Asp Gly Lys Glu His Leu Glu Glu Phe Thr
                340                 345                 350 atg ctg aac ttc tgc cag atg gga tcg gga tgc aca cgg gaa aat ctt      1104
Met Leu Asn Phe Cys Gln Met Gly Ser Gly Cys Thr Arg Glu Asn Leu
                355                 360                 365 gaa agc ata att aca gac ttc ctg aac cac ctg gga att gat ttc aag      1152
Glu Ser Ile Ile Thr Asp Phe Leu Asn His Leu Gly Ile Asp Phe Lys
                370                 375                 380 atc gta ggc gat tcc tgc atg gtc tat ggg gat acc ctt gat gta atg      1200
Ile Val Gly Asp Ser Cys Met Val Tyr Gly Asp Thr Leu Asp Val Met
385                 390                 395                 400 cac gga gac ctg gaa ctt tcc tct gca gta gtc gga ccc ata ccg ctt      1248
His Gly Asp Leu Glu Leu Ser Ser Ala Val Val Gly Pro Ile Pro Leu
                405                 410                 415 gac cgg gaa tgg ggt att gat aaa ccc tgg ata ggg gca ggt ttc ggg      1296
Asp Arg Glu Trp Gly Ile Asp Lys Pro Trp Ile Gly Ala Gly Phe Gly
                420                 425                 430 ctc gaa cgc ctt ctc aag gtt aaa cac gac ttt aaa aat atc aag aga      1344
Leu Glu Arg Leu Leu Lys Val Lys His Asp Phe Lys Asn Ile Lys Arg
                435                 440                 445 gct gca agg tcc ggg tct tac tat aac ggg att tct acc aac ctg taa      1392
Ala Ala Arg Ser Gly Ser Tyr Tyr Asn Gly Ile Ser Thr Asn Leu
                450                 455                 460

<210> SEQ ID NO 9
<211> LENGTH: 463
<212> TYPE: PRT
<213> ORGANISM: Methanosarcina mazeii

<400> SEQUENCE: 9

Met Asp Tyr Lys Asp Asp Asp Lys Met Asp Lys Lys Pro Leu Asn
1               5                   10                  15

Thr Leu Ile Ser Ala Thr Gly Leu Trp Met Ser Arg Thr Gly Thr Ile
                20                  25                  30

His Lys Ile Lys His His Glu Val Ser Arg Ser Lys Ile Tyr Ile Glu
                35                  40                  45

Met Ala Cys Gly Asp His Leu Val Val Asn Asn Ser Arg Ser Ser Arg
                50                  55                  60

Thr Ala Arg Ala Leu Arg His His Lys Tyr Arg Lys Thr Cys Lys Arg
65                  70                  75                  80
```

```
Cys Arg Val Ser Asp Glu Asp Leu Asn Lys Phe Leu Thr Lys Ala Asn
                 85                  90                  95
Glu Asp Gln Thr Ser Val Lys Val Lys Val Ser Ala Pro Thr Arg
            100                 105                 110
Thr Lys Lys Ala Met Pro Lys Ser Val Ala Arg Ala Pro Lys Pro Leu
            115                 120                 125
Glu Asn Thr Glu Ala Ala Gln Ala Gln Pro Ser Gly Ser Lys Phe Ser
130                 135                 140
Pro Ala Ile Pro Val Ser Thr Gln Glu Ser Val Ser Val Pro Ala Ser
145                 150                 155                 160
Val Ser Thr Ser Ile Ser Ser Ile Ser Thr Gly Ala Thr Ala Ser Ala
                165                 170                 175
Leu Val Lys Gly Asn Thr Asn Pro Ile Thr Ser Met Ser Ala Pro Val
            180                 185                 190
Gln Ala Ser Ala Pro Ala Leu Thr Lys Ser Gln Thr Asp Arg Leu Glu
        195                 200                 205
Val Leu Leu Asn Pro Lys Asp Glu Ile Ser Leu Asn Ser Gly Lys Pro
    210                 215                 220
Phe Arg Glu Leu Glu Ser Glu Leu Leu Ser Arg Arg Lys Lys Asp Leu
225                 230                 235                 240
Gln Gln Ile Tyr Ala Glu Glu Arg Glu Asn Tyr Leu Gly Lys Leu Glu
                245                 250                 255
Arg Glu Ile Thr Arg Phe Phe Val Asp Arg Gly Phe Leu Glu Ile Lys
            260                 265                 270
Ser Pro Ile Leu Ile Pro Leu Glu Tyr Ile Glu Arg Met Gly Ile Asp
        275                 280                 285
Asn Asp Thr Glu Leu Ser Lys Gln Ile Phe Arg Val Asp Lys Asn Phe
    290                 295                 300
Cys Leu Arg Pro Met Leu Ala Pro Asn Leu Tyr Asn Tyr Leu Arg Lys
305                 310                 315                 320
Leu Asp Arg Ala Leu Pro Asp Pro Ile Lys Ile Phe Glu Ile Gly Pro
                325                 330                 335
Cys Tyr Arg Lys Glu Ser Asp Gly Lys Glu His Leu Glu Glu Phe Thr
            340                 345                 350
Met Leu Asn Phe Cys Gln Met Gly Ser Gly Cys Thr Arg Glu Asn Leu
        355                 360                 365
Glu Ser Ile Ile Thr Asp Phe Leu Asn His Leu Gly Ile Asp Phe Lys
    370                 375                 380
Ile Val Gly Asp Ser Cys Met Val Tyr Gly Asp Thr Leu Asp Val Met
385                 390                 395                 400
His Gly Asp Leu Glu Leu Ser Ser Ala Val Val Gly Pro Ile Pro Leu
                405                 410                 415
Asp Arg Glu Trp Gly Ile Asp Lys Pro Trp Ile Gly Ala Gly Phe Gly
            420                 425                 430
Leu Glu Arg Leu Leu Lys Val Lys His Asp Phe Lys Asn Ile Lys Arg
        435                 440                 445
Ala Ala Arg Ser Gly Ser Tyr Tyr Asn Gly Ile Ser Thr Asn Leu
    450                 455                 460

<210> SEQ ID NO 10
<211> LENGTH: 18
<212> TYPE: DNA
<213> ORGANISM: Artificial Sequence
<220> FEATURE:
<223> OTHER INFORMATION: Linker DNA
```

<400> SEQUENCE: 10
agatcttcta gactcgag                                                              18

<210> SEQ ID NO 11
<211> LENGTH: 245
<212> TYPE: DNA
<213> ORGANISM: Artificial Sequence
<220> FEATURE:
<223> OTHER INFORMATION: tRNAVal-tRNA pyl tandem expression vector
<220> FEATURE:
<221> NAME/KEY: misc_feature
<222> LOCATION: (1)..(55)
<223> OTHER INFORMATION: Leader sequence
<220> FEATURE:
<221> NAME/KEY: misc_feature
<222> LOCATION: (216)..(245)
<223> OTHER INFORMATION: Terminator sequence
<220> FEATURE:
<221> NAME/KEY: misc_feature
<222> LOCATION: (129)..(146)
<223> OTHER INFORMATION: Linker sequence
<220> FEATURE:
<221> NAME/KEY: tRNA
<222> LOCATION: (56)..(128)
<223> OTHER INFORMATION: human tRNA valine
<220> FEATURE:
<221> NAME/KEY: tRNA
<222> LOCATION: (147)..(215)
<223> OTHER INFORMATION: M. mazei tRNA Pyl

<400> SEQUENCE: 11
agcgctccgg tttttctgtg ctgaacctca ggggacgccg acacacgtac acgtcgtttc      60
cgtagtgtag tggtcatcac gttcgcctaa cacgcgaaag gtccccggtt cgaaaccggg     120
cggaaacaag atcttctaga ctcgagggaa acctgatcat gtagatcgaa tggactctaa     180
atccgttcag ccgggttaga ttcccggggt ttccggacaa gtgcggtttt tttctccagc     240
tcccg                                                                 245

<210> SEQ ID NO 12
<211> LENGTH: 678
<212> TYPE: DNA
<213> ORGANISM: Artificial Sequence
<220> FEATURE:
<223> OTHER INFORMATION: Human Grb2 suppresion reporter gene
<220> FEATURE:
<221> NAME/KEY: CDS
<222> LOCATION: (1)..(678)
<223> OTHER INFORMATION:
<220> FEATURE:
<221> NAME/KEY: misc_feature
<222> LOCATION: (331)..(333)
<223> OTHER INFORMATION: Amber codon
<220> FEATURE:
<221> NAME/KEY: misc_feature
<222> LOCATION: (652)..(675)
<223> OTHER INFORMATION: FLAG tag

<400> SEQUENCE: 12

```
atg gaa gcc atc gcc aaa tat gac ttc aaa gct act gca gac gac gag       48
Met Glu Ala Ile Ala Lys Tyr Asp Phe Lys Ala Thr Ala Asp Asp Glu
1               5                   10                  15 ctg agc ttc aaa agg ggg gac atc ctc aag gtt ttg aac gaa gaa tgt       96
Leu Ser Phe Lys Arg Gly Asp Ile Leu Lys Val Leu Asn Glu Glu Cys
            20                  25                  30 gat cag aac tgg tac aag gca gag ctt aat gga aaa gac ggc ttc att      144
Asp Gln Asn Trp Tyr Lys Ala Glu Leu Asn Gly Lys Asp Gly Phe Ile
        35                  40                  45 ccc aag aac tac ata gaa atg aaa cca cat ccg tgg ttt ttt ggc aaa      192
```

```
              Pro Lys Asn Tyr Ile Glu Met Lys Pro His Pro Trp Phe Phe Gly Lys
                  50                  55                  60 atc ccc aga gcc aag gca gaa gaa atg ctt agc aaa cag cgg cac gat         240
Ile Pro Arg Ala Lys Ala Glu Glu Met Leu Ser Lys Gln Arg His Asp
65                  70                  75                  80 ggg gcc ttt ctt atc cga gag agt gag agc gct cct ggg gac ttc tcc         288
Gly Ala Phe Leu Ile Arg Glu Ser Glu Ser Ala Pro Gly Asp Phe Ser
                85                  90                  95 ctc tct gtc aag ttt gga aac gat gtg cag cac ttc aag gtg tag cga         336
Leu Ser Val Lys Phe Gly Asn Asp Val Gln His Phe Lys Val     Arg
            100                 105                 110 gat gga gcc ggg aag tac ttc ctc tgg gtg gtg aag ttc aat tct ttg         384
Asp Gly Ala Gly Lys Tyr Phe Leu Trp Val Val Lys Phe Asn Ser Leu
        115                 120                 125 aat gag ctg gtg gat tat cac aga tct aca tct gtc tcc aga aac cag         432
Asn Glu Leu Val Asp Tyr His Arg Ser Thr Ser Val Ser Arg Asn Gln
    130                 135                 140 cag ata ttc ctg cgg gac ata gaa cag gtg cca cag cag ccg aca tac         480
Gln Ile Phe Leu Arg Asp Ile Glu Gln Val Pro Gln Gln Pro Thr Tyr
145                 150                 155 gtc cag gcc ctc ttt gac ttt gat ccc cag gag gat gga gag ctg ggc         528
Val Gln Ala Leu Phe Asp Phe Asp Pro Gln Glu Asp Gly Glu Leu Gly
160                 165                 170                 175 ttc cgc cgg gga gat ttt atc cat gtc atg gat aac tca gac ccc aac         576
Phe Arg Arg Gly Asp Phe Ile His Val Met Asp Asn Ser Asp Pro Asn
                180                 185                 190 tgg tgg aaa gga gct tgc cac ggg cag acc ggc atg ttt ccc cgc aat         624
Trp Trp Lys Gly Ala Cys His Gly Gln Thr Gly Met Phe Pro Arg Asn
            195                 200                 205 tat gtc acc ccc gtg aac cgg aac gtc gac tac aag gac gac gat gac         672
Tyr Val Thr Pro Val Asn Arg Asn Val Asp Tyr Lys Asp Asp Asp Asp
        210                 215                 220 aag tga                                                                 678
Lys
```

<210> SEQ ID NO 13
<211> LENGTH: 17
<212> TYPE: DNA
<213> ORGANISM: Artificial Sequence
<220> FEATURE:
<223> OTHER INFORMATION: T7 promoter

<400> SEQUENCE: 13
taatacgact cactata                                                      17

<210> SEQ ID NO 14
<211> LENGTH: 248
<212> TYPE: DNA
<213> ORGANISM: Artificial Sequence
<220> FEATURE:
<223> OTHER INFORMATION: T7-tRNAPyl expression construct

<400> SEQUENCE: 14
ggggttccgc gcacatttcc ccgaaaagtg ccacctgacg tctaagaaac cattattatc       60
atgacattaa cctataaaaa taggcgtatc acgaggccct ttcgtcttca agaattcgcc      120
ctttaatacg actcactata gggagatctt ctagactcga gggaaacctg atcatgtaga      180
tcgaatggac tctaaatccg ttcagccggg ttagattccc ggggtttccg gacaagtgcg      240
gttttttt                                                              248

<210> SEQ ID NO 15

```
<211> LENGTH: 263
<212> TYPE: DNA
<213> ORGANISM: Artificial Sequence
<220> FEATURE:
<223> OTHER INFORMATION: T7-tRNATyr expression construct

<400> SEQUENCE: 15
ggggttccgc gcacatttcc ccgaaaagtg ccacctgacg tctaagaaac cattattatc      60
atgacattaa cctataaaaa taggcgtatc acgaggccct ttcgtcttca agaattcgcc     120
ctttaatacg actcactata gggagatctt ctagactcga gggtggggtt cccgagcggc     180
caaagggagc agactctaaa tctgccgtca tcgacttcga aggttcgaat ccttcccccca    240
ccagacaagt gcggtttttt ttt                                             263

<210> SEQ ID NO 16
<211> LENGTH: 26
<212> TYPE: DNA
<213> ORGANISM: Artificial Sequence
<220> FEATURE:
<223> OTHER INFORMATION: Forward primer

<400> SEQUENCE: 16
atgatatcag agggcctatt tcccat                                           26

<210> SEQ ID NO 17
<211> LENGTH: 27
<212> TYPE: DNA
<213> ORGANISM: Artificial Sequence
<220> FEATURE:
<223> OTHER INFORMATION: Reverse primer

<400> SEQUENCE: 17
tgctcgagaa gccaagaatc gaaatac                                          27

<210> SEQ ID NO 18
<211> LENGTH: 408
<212> TYPE: DNA
<213> ORGANISM: Artificial Sequence
<220> FEATURE:
<223> OTHER INFORMATION: PSE-tRNATyr expression construct

<400> SEQUENCE: 18
gatatcagag agataattag aattaatttg actgtaaaca caaagatatt agtacaaaat      60
acgtgacgta gaaagtaata atttcttggg tagtttgcag ttttaaaatt atgttttaaa     120
atggactatc atatgcttac cgtaacttga agtatttcg atttcttggc ttctcgagcc      180
ttgtggaaag gacgaaacac cgcttaaggg cccgttttc caagatcttc tagactcgag      240
ggtggggttc ccgagcggcc aaagggagca gactctaaat ctgccgtcat cgacttcgaa     300
ggttcgaatc cttcccccac cagacaagtg cggtttttt ctccagctcc cgaagcttgc      360
ggccgctttt tttttggagtt tcaaaagtag acagcggccg cagggccc                 408

<210> SEQ ID NO 19
<211> LENGTH: 34
<212> TYPE: DNA
<213> ORGANISM: Artificial Sequence
<220> FEATURE:
<223> OTHER INFORMATION: CMV-primer1

<400> SEQUENCE: 19
atcgaattct agttattaat agtaatcaat tacg                                  34

<210> SEQ ID NO 20
```

```
<211> LENGTH: 19
<212> TYPE: DNA
<213> ORGANISM: Artificial Sequence
<220> FEATURE:
<223> OTHER INFORMATION: CMV-primer2

<400> SEQUENCE: 20
agccttgtat cgtatatgc                                              19
```